US011410764B1

(12) United States Patent
Rosomoff et al.

(10) Patent No.: US 11,410,764 B1
(45) Date of Patent: Aug. 9, 2022

(54) SMART MEDICATION DISPENSER

(71) Applicant: Express Scripts Strategic Development, Inc., St. Louis, MO (US)

(72) Inventors: Peter A. Rosomoff, Wildwood, MO (US); Robert E. Hoffman, Linden, IN (US); Salvatore Anselmi, Nutley, NJ (US)

(73) Assignee: Express Scripts Strategic Development, Inc., St. Louis, MO (US)

(*) Notice: Subject to any disclaimer, the term of this patent is extended or adjusted under 35 U.S.C. 154(b) by 0 days.

(21) Appl. No.: 17/098,011

(22) Filed: Nov. 13, 2020

Related U.S. Application Data

(60) Provisional application No. 62/935,942, filed on Nov. 15, 2019.

(51) Int. Cl.
| | |
|---|---|
| *A61J 7/00* | (2006.01) |
| *G16H 20/13* | (2018.01) |
| *G16H 40/67* | (2018.01) |
| *G06K 7/10* | (2006.01) |
| *G06F 21/60* | (2013.01) |
| *G16H 10/60* | (2018.01) |

(52) U.S. Cl.
CPC ............ *G16H 20/13* (2018.01); *A61J 7/0076* (2013.01); *G06F 21/602* (2013.01); *G06K 7/10267* (2013.01); *G06K 7/10475* (2013.01); *G16H 10/60* (2018.01); *G16H 40/67* (2018.01); *A61J 2205/60* (2013.01)

(58) Field of Classification Search
CPC ...... A61J 7/0463; A61J 7/0076; A61J 7/0427; G16H 20/13
See application file for complete search history.

(56) References Cited

U.S. PATENT DOCUMENTS

| | | | |
|---|---|---|---|
| 3,762,601 | A | 10/1973 | McLaughlin |
| 3,998,356 | A | 12/1976 | Christensen |
| 4,275,384 | A | 6/1981 | Hicks |
| 4,473,884 | A | 9/1984 | Behl |
| 4,697,721 | A | 10/1987 | Johnson |

(Continued)

FOREIGN PATENT DOCUMENTS

| | | |
|---|---|---|
| CA | 2217220 C | 5/2001 |
| EP | 3469503 A2 | 4/2019 |

(Continued)

*Primary Examiner* — Timothy R Waggoner
(74) *Attorney, Agent, or Firm* — Dickinson Wright PLLC

(57) ABSTRACT

An aspect of the present disclosure is related to a medication dispensing device that includes a housing with an interior. A plurality of cartridge slots are located in the interior, and each of the cartridge slots includes a drive mechanism. A plurality of cartridges are removably disposed in respective ones of the cartridge slots. Each cartridge includes a stationary hub and a rotational wheel. The stationary hub has a window, and the rotational wheel has a plurality of medication chambers that contain medications. The rotational wheel is disposed in the stationary hub. The drive mechanism of the respective cartridge slot is operably connected with the drive wheel and is configured to rotate the rotational wheel relative to the stationary hub to selectively align the medication chambers with the window to dispense the medications contained in the medication chambers out of the cartridge.

23 Claims, 12 Drawing Sheets

(56) References Cited

U.S. PATENT DOCUMENTS

| | | | |
|---|---|---|---|
| 4,811,764 A | 3/1989 | McLaughlin | |
| 4,953,745 A * | 9/1990 | Rowlett, Jr. | G06Q 20/342 |
| | | | 221/5 |
| 5,148,944 A | 9/1992 | Kaufman | |
| 5,230,441 A | 7/1993 | Kaufman | |
| 5,372,276 A | 12/1994 | Daneshvar | |
| 5,472,113 A * | 12/1995 | Shaw | A61J 7/0084 |
| | | | 221/15 |
| 5,582,323 A | 12/1996 | Kurtenbach | |
| 6,175,779 B1 | 1/2001 | Barrett | |
| 6,253,953 B1 | 7/2001 | Ishizuka | |
| 6,259,654 B1 | 7/2001 | De La Huerga | |
| 6,510,962 B1 | 1/2003 | Lim | |
| 6,662,081 B1 | 12/2003 | Jacober | |
| 6,874,612 B1 | 4/2005 | Uland | |
| 6,941,948 B2 | 9/2005 | Staniforth | |
| 6,962,035 B2 | 11/2005 | Yamamoto | |
| 7,584,849 B2 | 9/2009 | Mauk | |
| 8,452,446 B1 | 5/2013 | Madris | |
| 9,078,983 B2 | 7/2015 | Herr | |
| 9,245,093 B2 | 1/2016 | Shaw | |
| 9,251,493 B2 | 2/2016 | Jacobs | |
| 9,323,897 B2 | 4/2016 | Horst | |
| 9,498,408 B2 | 11/2016 | Lehmann | |
| 9,675,523 B2 | 6/2017 | Ducatt | |
| 10,022,305 B2 | 7/2018 | Bunker | |
| 10,258,749 B2 | 4/2019 | Schoonmaker | |
| 10,512,592 B1 * | 12/2019 | Sandhu | A61J 1/1437 |
| 10,583,941 B2 | 3/2020 | Holmes | |
| 10,689,270 B2 | 6/2020 | Tikalsky | |
| 10,993,881 B1 | 5/2021 | Karpman | |
| 2005/0049747 A1 | 3/2005 | Willoughby | |
| 2006/0184271 A1 | 8/2006 | Loveless | |
| 2008/0054007 A1 | 3/2008 | Mador | |
| 2010/0228566 A1 | 9/2010 | Taylor | |
| 2011/0125315 A1 * | 5/2011 | Handfield | A61J 7/0084 |
| | | | 700/231 |
| 2011/0231006 A1 | 9/2011 | Saltsov | |
| 2014/0244033 A1 | 8/2014 | Ucer | |
| 2014/0358278 A1 | 12/2014 | Zhang | |
| 2015/0148943 A1 | 5/2015 | Sullivan | |
| 2015/0283036 A1 | 10/2015 | Aggarwal | |
| 2015/0310185 A1 | 10/2015 | Shah | |
| 2016/0042150 A1 | 2/2016 | Moloughney | |
| 2016/0075460 A1 | 3/2016 | Despa | |
| 2016/0158108 A1 | 6/2016 | Gofer | |
| 2016/0324727 A1 * | 11/2016 | Waugh | G16H 20/13 |
| 2017/0193191 A1 | 7/2017 | Blum | |
| 2019/0035499 A1 | 1/2019 | Daya | |
| 2019/0228852 A1 | 7/2019 | García | |
| 2019/0326006 A1 | 10/2019 | Arric | |
| 2020/0085686 A1 * | 3/2020 | Aliakbarian | G07C 9/257 |
| 2020/0085694 A1 | 3/2020 | Patel | |
| 2020/0165014 A1 | 5/2020 | Holmes | |
| 2020/0279630 A1 | 9/2020 | Gersten | |
| 2020/0290897 A1 | 9/2020 | Tikalsky | |
| 2020/0323738 A1 * | 10/2020 | Bear | A61J 7/0084 |

FOREIGN PATENT DOCUMENTS

| | | |
|---|---|---|
| GB | 2122578 B | 10/1985 |
| WO | 2018031724 A1 | 2/2018 |

* cited by examiner

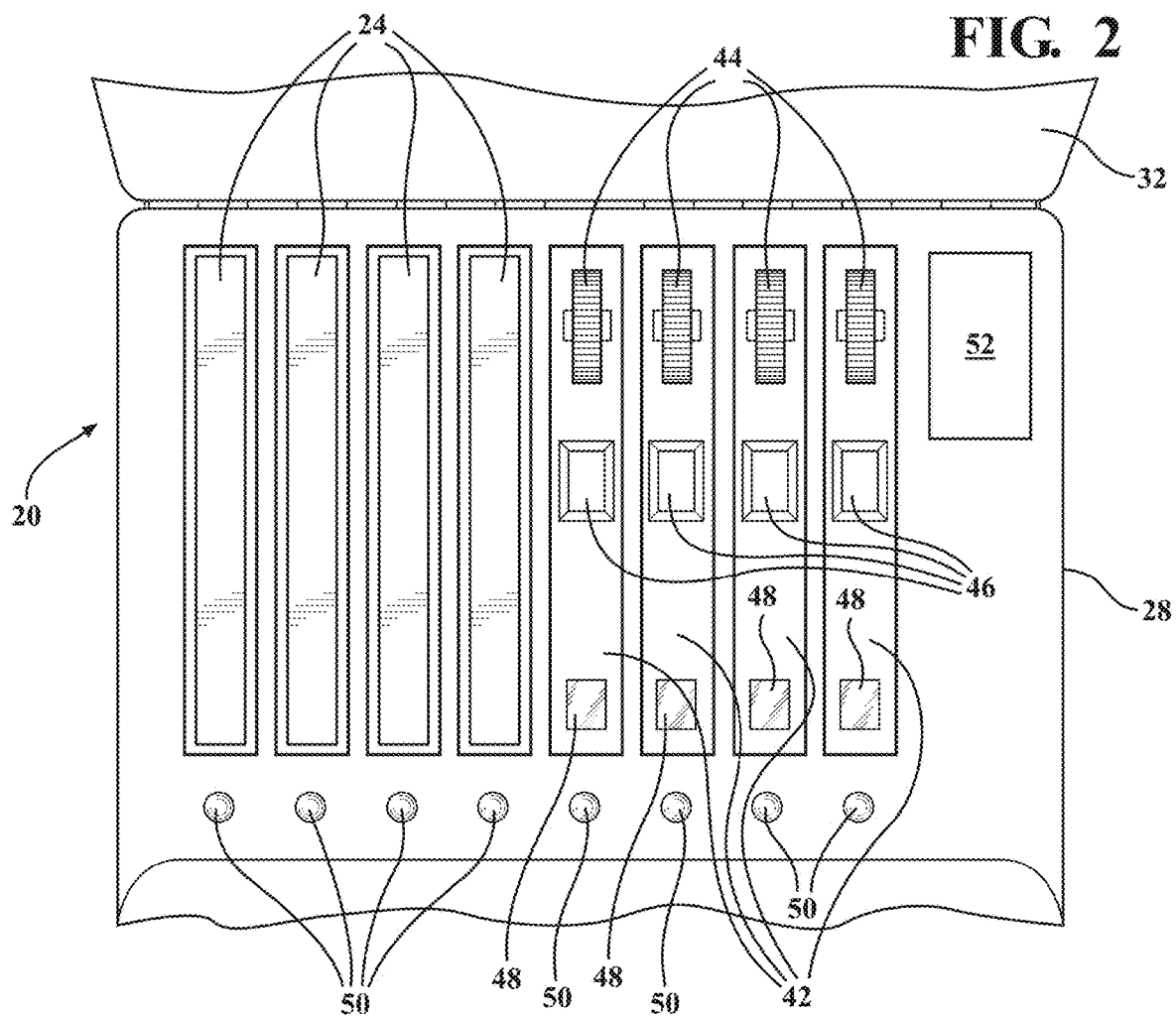
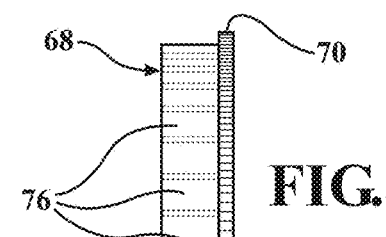
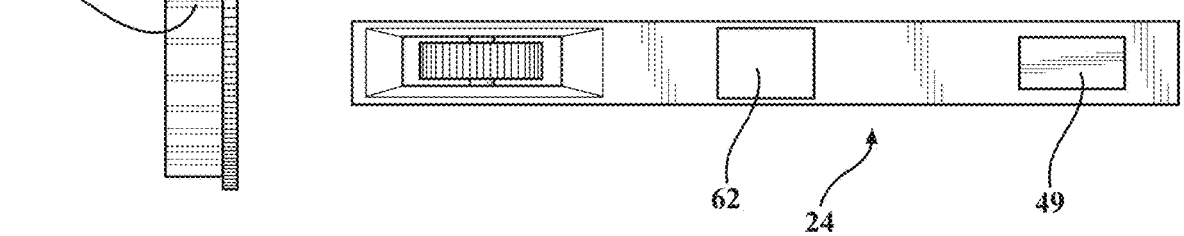

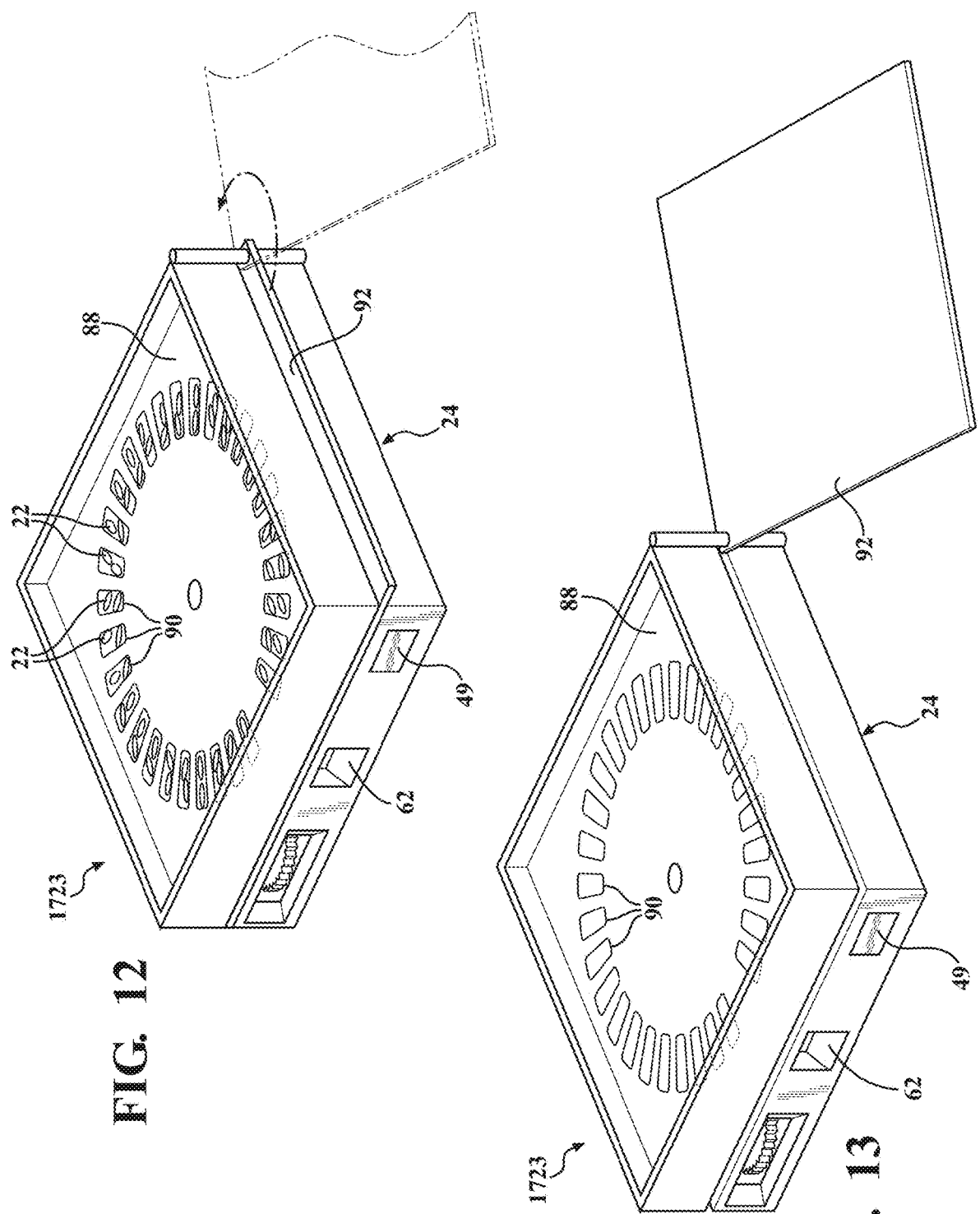

SMART MEDICATION DISPENSER

CROSS-REFERENCE TO RELATED APPLICATION

This application claims priority to and the benefit of U.S. Provisional Application Ser. No. 62/935,942, filed on Nov. 15, 2019, entitled "SMART PILL DISPENSER", the contents of which are herein incorporated by reference.

FIELD OF THE INVENTION

1. Field of the Invention

The present invention is related generally to a medication dispensing device which contains multiple different types of medications and can dispense those medications to a user.

BACKGROUND

One known product that is designed to improve medication compliance is a multi-chamber pill container that includes a plurality of individual chambers that can contain the same or different types of medications arranged according to dosages, i.e., a first does is in the first chamber, a second dose is in the second chamber, etc. Such pill containers need to be filled and operated manually. Another known product includes a series of blister packs that individually contain dosages of medications. Such blister packs can also contain personalized dosages but are generally filled in a pharmaceutical setting.

SUMMARY OF THE INVENTION

An aspect of the present disclosure is related to a medication dispensing device that includes a housing with an interior. A plurality of cartridge slots are located in the interior, and each of the cartridge slots includes a drive mechanism. A plurality of cartridges are removably disposed in respective ones of the cartridge slots. Each cartridge includes a stationary hub and a rotational wheel. The stationary hub has a window, and the rotational wheel has a plurality of medication chambers that contain medications. The rotational wheel is disposed in the stationary hub. The drive mechanism of the respective cartridge slot is operably connected with the drive wheel and is configured to rotate the rotational wheel relative to the stationary hub to selectively align the medication chambers with the window to dispense the medications contained in the medication chambers out of the cartridge.

In an example embodiment, the rotational wheel of each cartridge includes a plurality of teeth, and the drive mechanism of each cartridge slot includes an increment gear that is mechanically coupled with the teeth of the rotational wheel for driving rotation of the rotational wheel relative to the stationary hub.

In an example embodiment, the drive mechanism of each cartridge slot further includes an electric motor.

In an example embodiment, the rotational wheel includes a plurality of radially extending wall that are circumferentially spaced apart from one another by the medication chambers.

In an example embodiment, the stationary hub of each cartridge includes a non-circular tab that is received in a similarly shaped opening of the cartridge slot to orient the window in a vertically downward direction.

In an example embodiment, the medication dispensing device further includes a memory that contains data related to an automatic dispensing schedule and includes a processor that is configured to control rotation of the increment gear to rotate the rotational wheel and dispense the medications from the cartridge according to the automatic dispensing schedule.

In an example embodiment, the housing further includes a dispensing chute that guides the medications dispensed out of the cartridges through the windows to a dispensing tray.

In an example embodiment, each of the cartridges has a chip that includes data corresponding to the contents of the cartridge and the housing includes a chip reader that is configured to read the data on the chip.

In an example embodiment, the medication dispensing device further includes a wireless module for communicating with an external device.

Another aspect of the present disclosure is related to a medication dispensing device that includes a housing, which has an interior with a plurality of cartridge slots. Each of the cartridge slots includes a drive mechanism. A plurality of cartridges are removably disposed in the cartridge slots. Each of the cartridges includes a rotational wheel that is operably connected with the drive mechanism of the cartridge slot. The rotational wheel includes a plurality of medication chambers that are circumferentially spaced apart from one another and that contain medications. A processor is configured to selectively and individually activate the drive mechanisms of the cartridge slots to selectively dispense medications out of any of the cartridges contained in the cartridge slots.

In an example embodiment, the processor is configured to dispense medications out of the cartridges according to either an automatic dispensing schedule or in response to a demand.

In an example embodiment, each cartridge includes a chip containing data, and the data is encrypted and is configured to only be read by the medication dispensing device associated with a patient.

In an example embodiment, the medication dispensing system further includes an identification verification system that is configure to only allow medications to be dispensed from the cartridges in response to a positive verification of a user.

In an example embodiment, the identification verification system includes at least one sensor on either the dispensing device or an external device that is in electrical connection with the dispensing device.

According to another aspect of the present disclosure, a method of dispensing a medication to a user is provided. The method includes the step of inserting at least one cartridge into one of a plurality of cartridge slots within a housing of a medication dispensing device. The at least one cartridge includes a stationary hub and a rotation wheel. The rotational wheel includes a plurality of circumferentially spaced apart chambers including medication doses. The method proceeds with the step of reading data contained on the at least one cartridge and storing in a memory of the dispensing device information related to the medication doses. The method continues with the step of receiving with a processor an instruction to dispense a medication dose from the at least one cartridge. The method proceeds with rotating the rotational wheel of one of the cartridges with a drive mechanism to vertically align one of the chambers with a medication drop door causing the medication dose in the chamber that is now aligned with the medication drop door to fall out of the cartridge.

In an example embodiment, the method further includes the step of verifying an identity of a user after the step of receiving the instruction with the processor, and the step of rotating the rotational wheel is proceeded to only in response to a positive verification of the identity of the user.

In an example embodiment, the step of inserting at least one cartridge into one of a plurality of cartridge slots is further defined as inserting at least two cartridges into at least two cartridge slots.

In an example embodiment, at least one of the cartridges is associated with a first user and at least one of the cartridges is associated with a different second user, and the step of verifying the identity of the user includes verifying that the user is the user associated with the cartridge to be dispensed from.

In an example embodiment, the instruction to dispense a medication dose from one of the cartridges is according to an automatic dispensing schedule that is recorded in a memory of the medication dispensing device.

In an example embodiment, the automatic dispensing schedule is downloaded to the memory from the chip on the at least one cartridge.

BRIEF DESCRIPTION OF THE DRAWINGS

These and other features and advantages of the disclosure will become more readily appreciated when considered in connection with the following description of the presently preferred embodiments, appended claims and accompanying drawings, in which:

FIG. 2 is a top elevation and fragmentary view of the first exemplary embodiment of the medication dispensing device and with a lid of the medication dispensing device being in an open position;

FIG. 5 is a side elevation view of a rotational wheel of an exemplary embodiment of the cartridge;

FIG. 6 is a bottom elevation view of an exemplary cartridge;

FIG. 12 is a perspective view showing the fill plate of FIG. 11 and showing a cartridge to be filled positioned below the fill plate and showing a gate in a closed position;

FIG. 13 is another perspective view showing the fill plate of FIG. 11 and showing the gate in an open position and showing a cartridge that is filled with medications;

DESCRIPTION OF THE ENABLING EMBODIMENT

Figure 1:
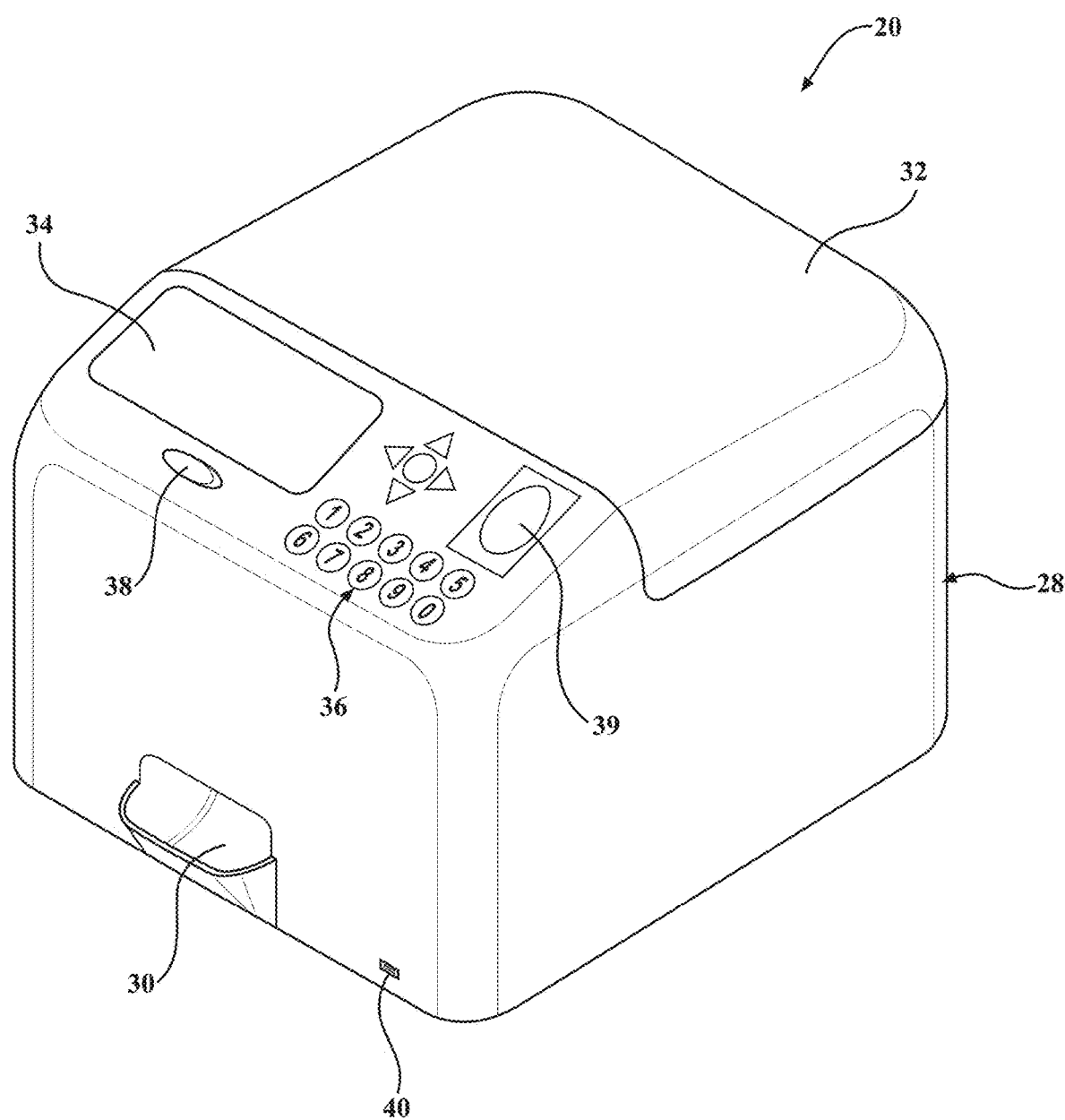
FIG. 1 is a perspective view of a first exemplary embodiment of a medication dispensing device.

Referring to the Figures, wherein like numerals indicate corresponding parts throughout the several views, one aspect of the present invention is related to a medication dispensing device 20 that is configured to automatically dispense one or more different types of solid medications 22 to a user (e.g., a patient, a caregiver or the like). The dispensing device 20 is conveniently contained within a compact package, which can be stored in a convenient location within a user's house, such as on a kitchen counter, under a shelf, or on a bedside table. The medications contained in the dispensing device 20 are hereinafter frequently referred to as pills 22; however, it should be appreciated that other types of solid medications (such as tablets, gel caps, capsules or the like, e.g., non-liquid medicines) may be employed. As discussed in further detail below, in operation, the dispensing device 20 automatically dispenses a predetermined dosage of pills 22 directly out of one or more medication cartridges 24 either according to a pre-set schedule or upon receiving an on demand request from the user. This improves medication compliance by allowing the user to conveniently store a large supply of different pills 22 in a single, convenient device 20, which not only stores the pills 22 in a sorted manner but also assists the user with their medication schedule, thereby preventing either missed or double doses. As also discussed in further detail below, the medication dispensing device 20 is a smart device in that it knows what types of pills 22 are contained within it and the quantities of those pills 22 and is able to communicate this and other information to a user's external device 26 and is able to receive information from the external device 26. The external device 26 may be, for example, a smart phone, a tablet, a personal, computer, a smart watch, a dedicated unit, a voice assistance, a host, or any suitable type of electronic device. The cartridges 24 in the dispensing device 20 may contain a range of different types of pills 22 including both prescription and non-prescription medications. As discussed in further detail below, the dispensing device 20 may also communicate with other authorized devices, e.g., a caregiver device, a family member device and the like. This can work to notify others of any or all dispensing events.

The dispensing device 20 includes a housing 28 with an open interior and a dispensing tray 30. A lid 32 is hingedly connected with the housing 28 and can be manually or automatically opened and closed. The housing 28 and lid 32 are sealed against one another to block all or substantially all outside light from entering the open interior, thereby controlling the environment within the open interior. The lid 32 is shown on the top of the housing 28 but may also be positioned on the side or rear of the housing 28. The cartridges 24 are removably contained in the open interior and can be accessed by opening the lid 32.

A front side surface of the housing 28 includes machine-to-human interaction devices or a human machine interface (HMI). Four such devices are a display screen 34, a keypad 36, at least one button 38, and a verification device (such as a fingerprint scanner 39). The display screen 34 may be, for example, a liquid crystal display (LCD) or light emitting diode (LED) display and may include a touch screen interface. However, any suitable screen type may be employed. The display screen 34 and keypad 38 allow a user to, inter alia, check the quantities and types of medications contained in the dispensing device 20; adjust an automatic dispensing schedule; and/or pair the dispensing device with the external device 26. When the dispensing device 20 determines that the medication count in any of the cartridges 24 is below a predetermined threshold (e.g., a week or two of medication doses remains), an alert can be displayed on the display screen 34. In the exemplary embodiment, the at least one button 38 is a dispense button 38 for requesting an immediate release of a dosage of pills 22 from one of the cartridges 24. The user can use the keypad 36, the display screen 34, or the external device 26 to select which of the cartridges 24 in the dispensing device 20 releases the medication dose upon activation of the dispense button 38. The dispensing device 20 may also include a speaker and/or a microphone to provide other means by which the user can interact with the dispensing device 20 to perform any of the aforementioned operations. The fingerprint scanner 39 (or other verification device) functions to verify a user's identity prior to dispensing any pills 22 or certain types of pills 22 in a manner described in further detail below. The housing 28 further includes an electronic communication port, such as a universal serial bus (USB) port 40, for communicating with the external device 26 in a non-wireless manner. Other types of electronic communication ports may alternately or additionally be included.

The interior of the housing 28 includes a plurality of cartridge slots 42 that can removably hold a plurality of cartridges 24. In the exemplary embodiment, the housing 28 includes eight cartridge slots 42 with four of the cartridge slots 42 containing respective cartridges 24 and with four of the cartridge slots 42 being empty and ready to receive cartridges 24. As discussed in further detail below, the cartridges 24 can be inserted into and removed from the cartridge slots 42 in a quick and easy manner by the user without any special tools. The cartridge slots 42 are preferably configured such that proper insertion of a cartridge 24 therein results in an audible "snapping" sound to provide the user with a positive affirmation that the insertion was successful. In other embodiments, the housing 28 may contain more or fewer than eight cartridge slots 42. Cartridges 24 containing any combination of the same or different types of medications can be disposed in any combination of the cartridge slots 42.

In the exemplary embodiment, each cartridge slot 42 includes an increment gear 44, a pill drop door 46, a data reader 48, and a refill indicator light 50. As discussed in further detail below, these components can all be controlled by a processor 1500 that will execute instructions to control these components using instructions stored in a memory 1504, sensed information from the components, and information downloaded from external data sources, e.g., servers.

The increment gear 44 is a part of a drive mechanism that also includes an actuator, such as an electric motor 1502, for activating the cartridge 24 contained in the respective cartridge slot 42 to release a dose of medication, which may include one or more pills 22. Upon release of pill(s) 22 from the cartridge 24, the pill drop door 46 guides the pill(s) 22 into a dispensing chute 51, which guides the pill(s) 22 into the dispensing tray 30, as discussed in further detail below. The increment gear 44 may take a range of different forms including those of a spur gear or a worm gear.

In the exemplary embodiment, the data reader 48 is a chip reader 48 that is configured to read data contained on a chip 49, which is found on the packaging of the cartridge 24. The data may be contained on a memory, such as an electronic memory or a magnetic memory, that is embedded within the chip 49 on the packaging. The data preferably includes: (1) drug name and strength; (2) medication count; (3) physician instructions; (4) refill date; (5) dispense date; (6) expiration date, etc. Additional data may also be included in the chip 49. The chip 49 may be of the contact or wireless type, such as a Radio-Frequency Identification (RFID) chip or a chip that communicates via cellular protocols. In an example embodiment, the data contained on the chip 49 is encrypted, and the processor 1500 in the dispensing device 20 can decrypt the data stored in the chip 49. In one embodiment, the encryption can be configured such that the data on the chip 49 can only be read by a single dispensing device 20, i.e., the one associated with the patient that the cartridge 24 is prescribed to. This ensures that only the correct person can access the pills 22 contained in the cartridge 24 by preventing another person's dispensing device from dispensing medications from the cartridge 24.

In other embodiments, the cartridge 24 packaging may contain a unique code that can be read by the data reader 48 and that instructs the dispensing device 20 as to the contents of the cartridge 24. Such a code could be provided in the form of, for example, a barcode, or a quick-response (QR) Code. In these embodiments, the data reader 48 has the appropriate form to read the code, e.g., a barcode scanner or a QR code scanner. The dispensing device 20 can use the unique code to determine the type and quantity of the medication in the cartridge 24 by referencing a database, which may be stored on an internal memory 1504 of the dispensing device 20 or on an external server that may be remote from the dispensing device 20 and only accessible via the internet 1600.

In operation, when the dispensing device 20 determines that the medication count in one of the cartridges 24 is below a predetermined threshold (e.g., less than a week of less of medication remaining), the refill indicator light 50 associated with the cartridge slot 42 containing that cartridge 24 turns on to alert the user that the replacement of the cartridge 24 will be required soon if the medication contained therein is to be continued. The display screen 34 can also provide an alert or the alert can be provided to the user through another means, such as an audible alert through the speaker or a notification on the external device 26. Similarly, if the dispensing device determines that the pills 22 in any of the cartridges 24 are approaching their expiration dates or have been recalled by their manufacturers, the refill indicator 50 associated with the appropriate cartridge slot 42 turns on to alert the user that replacement of the cartridge 24 will be required immediately or soon if the medication contained therein is to be continued. In all of these cases, the dispensing device 20 may provide the user with alerts through other ways, such as on the display screen 24 or on the external device 26. The alert could include, for example, a phone number to call or a directly link to contact a pharmacy or medical care provider to refill the medication.

The dispensing device 20 is preferably powered by alternating current (AC) from a wall outlet as its primary power source but contains a battery backup 52 so that operation continues in the event of a loss of power from the primary power source. The battery backup 52 may be a removeable or non-removeable rechargeable battery pack or it may be one or more disposable battery cells.

Referring now to FIGS. 5-10, an exemplary embodiment of one of the cartridges 24 is shown. The cartridge 24 is comprised of two main pieces: a stationary hub 54 and a rotational wheel 56. These pieces are each preferably made of a polymeric material, e.g., plastic, and are shaped through an injection molding operation. However, other materials (e.g., metal, alloys or other rigid materials) and manufacturing operations may be employed.

Figure 8:
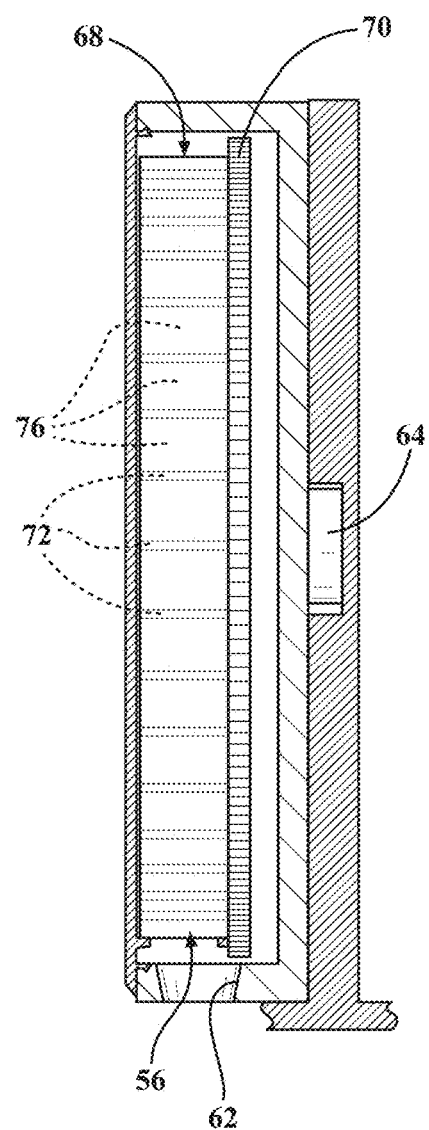
FIG. 8 is a partially cross-sectional view showing the exemplary cartridge disposed in a cartridge slot of the first exemplary embodiment of the medication dispensing device.
Figure 9:
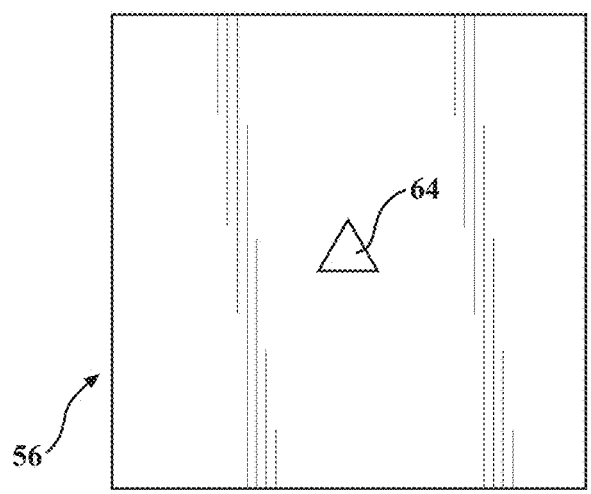
FIG. 9 is a back elevation view of a stationary hub of the exemplary cartridge.
Figure 10:
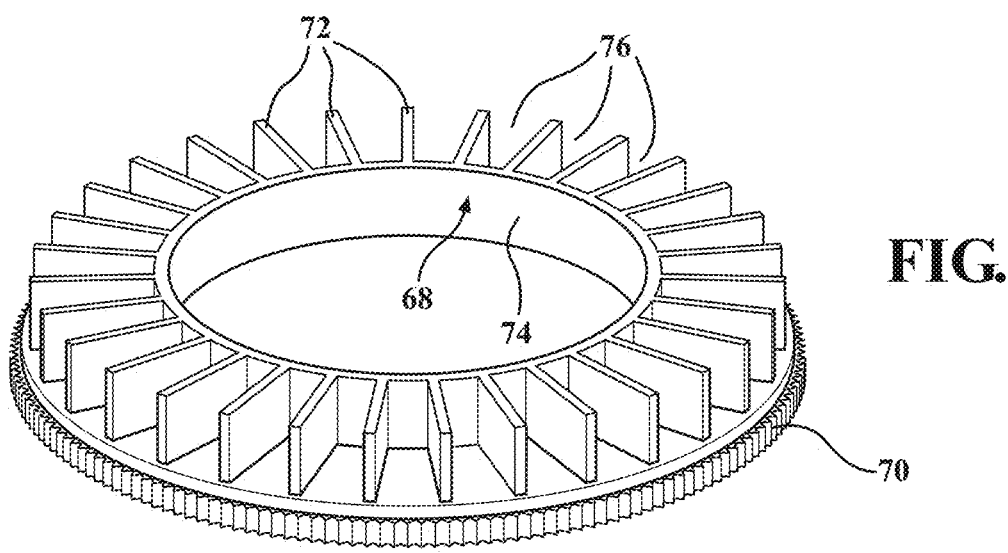
FIG. 10 is a perspective view of the exemplary rotational wheel.

The stationary hub 54 has a cylindrically shaped opening with a flat bottom 58 and a side wall 60. The rotational wheel 56 is disposed in the cylindrically shaped opening and is rotatable relative to the stationary hub 54 within the opening. The side wall 60 does not extend through a full circle but rather has a gap, or window 62, formed into it. The stationary hub 54 also has an outer surface that faces away from the rotational wheel 56 and that has a centrally located tab 64, which has a non-circular in shape (e.g., a key, a 3D polygon or the like). As shown in FIG. 8, when the cartridge 24 is inserted into the cartridge slot 42, the tab 64 is inserted into a correspondingly shaped opening (e.g., a keyhole) on a vertical wall of the cartridge slot 42 to hold the stationary hub 54 in place with the window 62 facing vertically downwardly.

The rotational wheel 56 has a container portion 68 and a gear portion 70. The container portion 68 has a generally circular outer perimeter and is sized to fit within the confines of the circular side wall 58 of the stationary hub 54, i.e., the side wall 58 has an inner diameter that is slightly greater than an outer perimeter of the container portion 68. In one embodiment, the container portion 68 has an approximately nine-inch (9 in) diameter. In other embodiments, the container portion 68 may be either smaller or larger than nine inches in diameter. The gear portion 70 includes a plurality of gear teeth extending along its periphery for mechanical engagement with a drive mechanism in the dispensing device 20 to rotate the rotational wheel 56 to dispense pills 22 therefrom during operation of the dispensing device 20.

Figure 3:
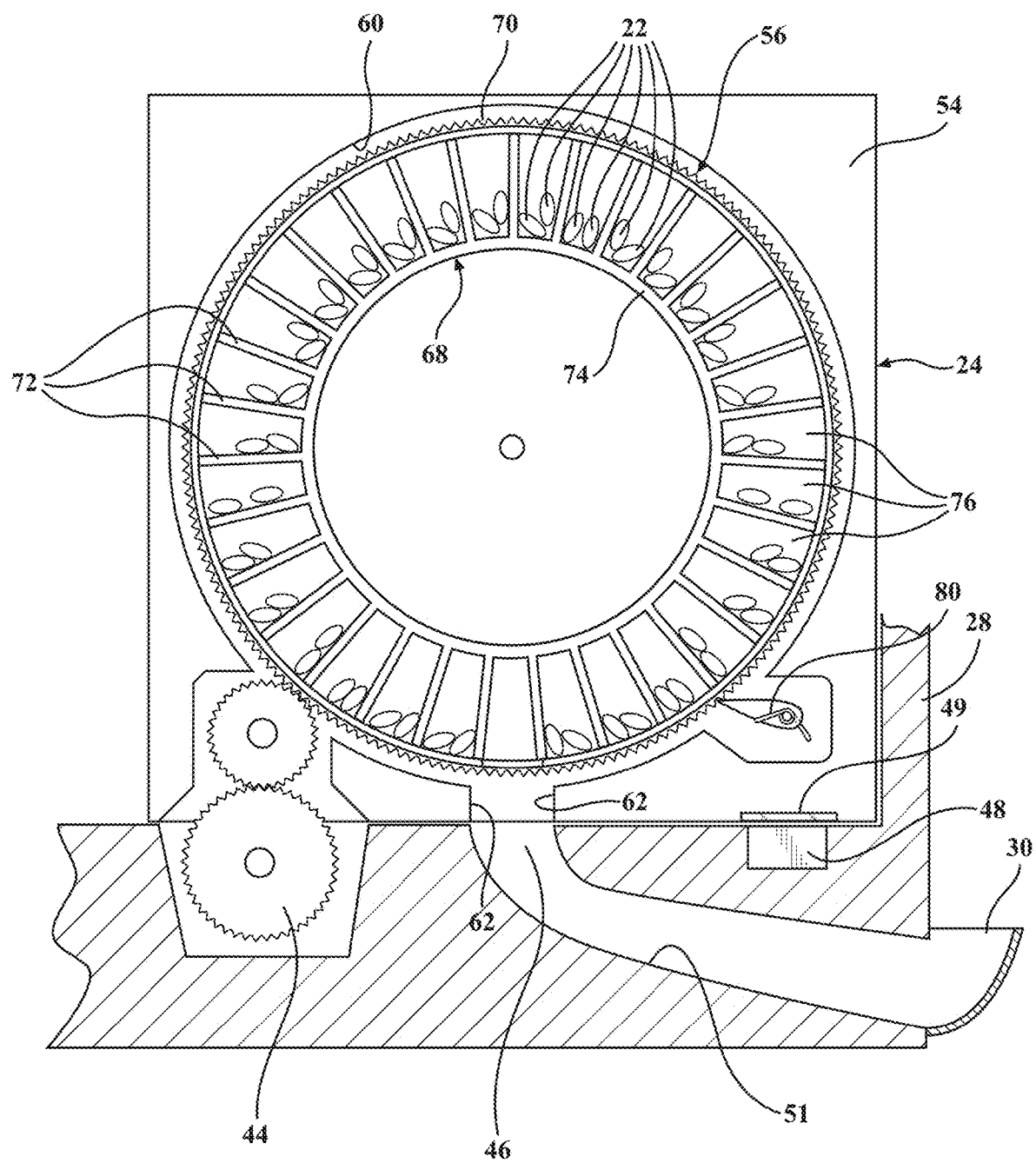
FIG. 3 is a partially cross-sectional view showing a cartridge disposed in the first exemplary embodiment of the medication dispensing device.
Figure 4:
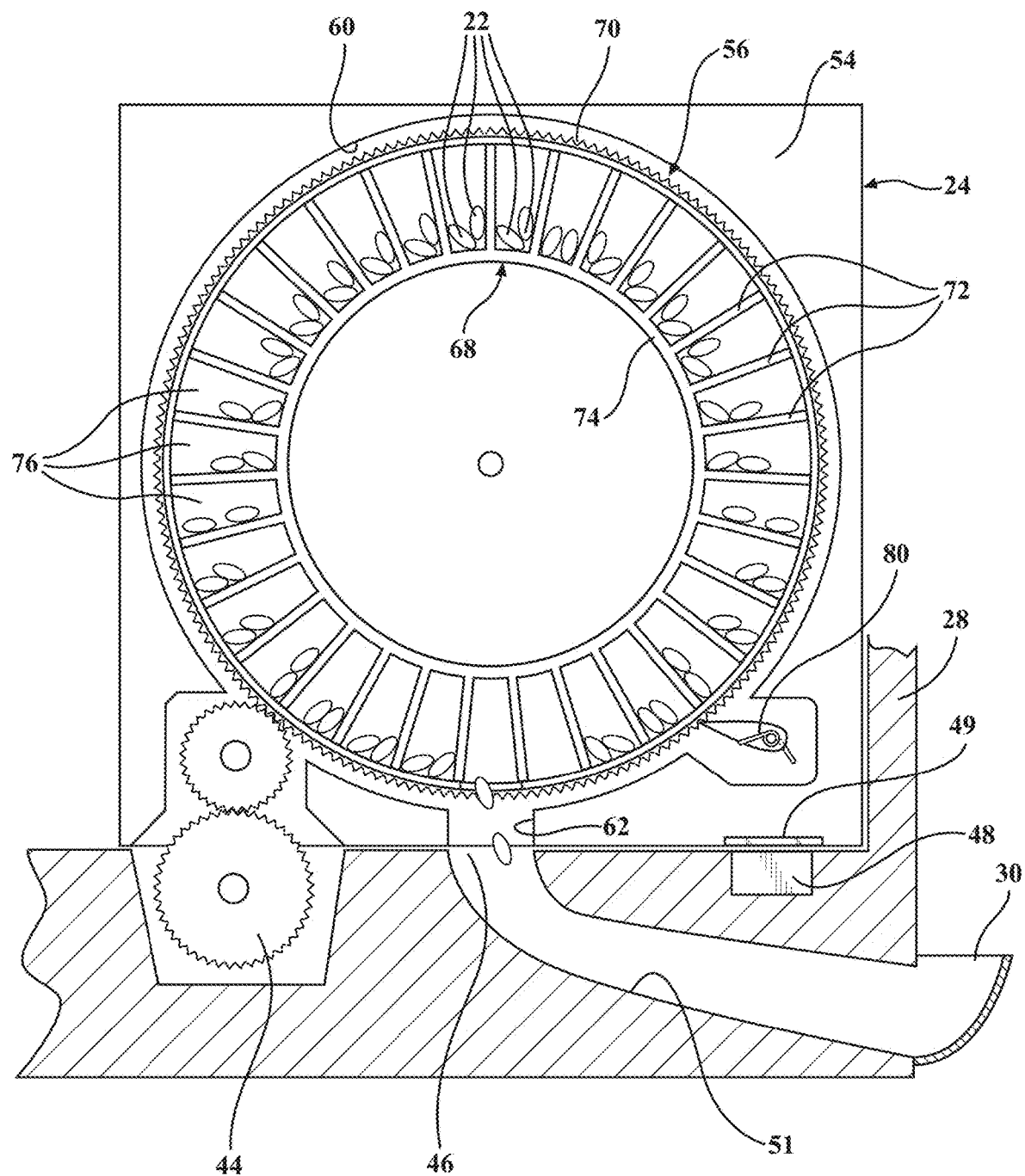
FIG. 4 is another partially cross-sectional view showing a cartridge disposed in the first exemplary embodiment of the medication dispensing device and during a dispensing operation.
Figure 7:
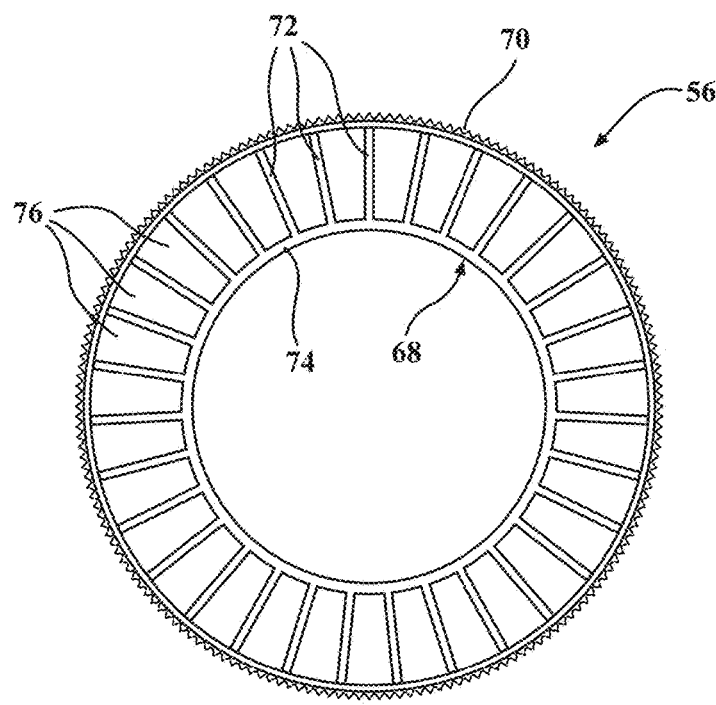
FIG. 7 is a front elevation view of the rotational wheel of FIG. 5.

The rotational wheel 56 includes a plurality of radially radial walls 72 that extend from a circular inner wall 74 and are separated from one another by a plurality of distinct pill chambers 76 that can each contain a dose of medication, which may include one or more pills 22 (FIGS. 3 and 4 show the pills 22 in the chambers 76) that can either be the same type of medication or a different type of medication. Due to the radial extension of the radial walls 72, the pill chambers 76 are all generally wedge, or pizza slice, shaped. In the exemplary embodiment, the radial walls 72 are equally spaced apart from one another such that the pill chambers 76 all have the same shape and size. More particularly, in the exemplary embodiment, adjacent radial walls 72 are angled relative to one another by approximately 12.7° such that the rotational wheel 56 has enough pill chambers 76 to store a thirty (30) day supply of a medication doses plus one empty chamber 76 that is intentionally without pills 22 and that is aligned with the window 62 of the stationary hub 54 after the cartridge 24 is filled and prior to it being inserted into the dispensing device 20. Initially aligning the empty chamber 76 with the window 62 allows the cartridge 24 to be handled prior to insertion into the dispensing device 20 without any of the pills 22 falling out of the other pill chambers 76.

In another embodiment, the radial walls 72 are angled relative to one another by approximately 7.8° so that the rotational wheel 56 has enough pill chambers 76 to store a forty-five (45) day supply of medication plus one empty pill chamber 76. In other embodiments, the rotational wheel 56 could be provided with more or fewer pill chambers 76, and the radial walls 72 may be spaced apart from one another by variable distances such that at least some of the pill chambers 76 have different sizes to accommodate different medication doses. In some embodiments, the rotational wheel 56 may lack the circular inner wall 74 and the radial walls 72 may all extend to a common central location.

The pills 22 may be contained in the pill chambers 76 of the rotational wheel 56 either loosely or in individual dose packages. In some embodiments, the same types and quantities of pills 22 may be contained in all of the pill chambers 76. In other embodiments, the cartridge 24 may be customized to a person's specific medication regimen by including different medication dosages (e.g., either different pills 22 or different quantities of pills 22) in different pill chambers 76. In some embodiments, at least two different types of pills 22 may be disposed in one or more of the pill chambers 76.

During assembly of the cartridge 24, the pills 22 are loaded into the pill chambers 76, such as with the equipment and according to the process described in further detail below. Next, a cap may be fitted to the stationary hub 54 to trap the rotational wheel 56 with the pills 22 within the stationary hub 54. A radial gap between each of the outer edges of the radial walls 72 of the rotational wheel 56 and the side wall 60 of the stationary hub 54 is preferably no greater than one eighth of an inch (⅛") and is preferably approximately one sixteenth of an inch (1/16") to ensure that even the smallest pills 22 are not able to pass through this gap from one pill chamber 76 to an adjacent pill chamber 76. The stationary hub 54 and the rotational wheel 56 may be fixed together against relative rotation, such as with a pawl 80, so that the cartridge 24 can be handled or shipped without the pills 22 falling out therefrom.

As shown in FIGS. 3 and 4, when the cartridge 24 is installed in the cartridge slot 42, teeth on the increment gear 44 are mechanically connected with teeth on the outer periphery of the gear portion 70 of the rotational wheel 56. This mechanical connection between the increment gear 44 and the gear portion 70 of the rotational wheel 56 may either be direct or may be via one or more intermediate gears. The non-rotationally symmetrical shape of the tab 64 ensures that the window 62 of the side wall of the stationary hub 54 remains aligned with the pill drop door 46 as the rotational wheel 56 is driven in rotation by the increment gear 44.

In operation, activation of the electric motor 1502 (shown in FIG. 15) in respond to a command (either according to a manual demand or an automatic dispensing schedule) to dispense a dosage of pill(s) 22 from the cartridge 24 rotates the increment gear 44 to turn the rotational wheel 56 about a horizontally extending axis while the stationary hub 54 remains fixed with the housing 28. This brings a next sequential one of the pill chambers 76 into alignment with the pill drop door 46. Gravity then pulls any pill(s) 22 in the pill chamber 76 out of the pill chamber 76 and into the dispensing chute 51, which conveys those pill(s) 22 to the dispensing tray 30. The housing 28 may include a single dispensing chute 51 with a funnel shape that can receive pills 22 from all of the cartridges 24 or may include multiple dispensing chutes 51 all leading to a common dispensing tray 30.

The teeth on the gear portion 70 of the rotational wheel 56 are disposed at a fine pitch to allow for the rotation of the rotational wheel 56 to be very precisely controlled. The location of the teeth on the outer periphery of the rotational wheel 56 has been found to allow for very precise movements of the rotational wheel 56, thereby preventing unintentional double dispensing (dispensing the contents of two pill chambers 76 when only one should be dispensed) or missed dispensing (when the rotational wheel 56 does not rotate enough to dispense a dosage of pills 22).

The spring-loaded pawl 80 cooperates with the gear teeth on the rotational wheel 56 to restrict unintentional rotation of the rotational wheel 56. In the event of a loss of power or a malfunction of the dispensing device 20, an access door may be provided on the cartridge 24 to allow the user to access and manually disengage the pawl 80 and manually rotate the rotational wheel 56 until a dosage of pill(s) 22 is dispensed therefrom. In some embodiments, the pawl 80 may be a component of the cartridge slot 42 of the dispensing device 20 rather than of the cartridge 24.

The dispensing device 20 can operate with cartridges 24 occupying any number and any combination of the cartridge slots 42. When properly installed in the cartridge slots 42, the cartridges 24 are oriented such that their respective central axes, about which the respective rotational wheels 56 rotate, all are oriented horizontally and are co-axially aligned with one another. For each cartridge 24, the shape of the tab 64 on the stationary hub 54 ensures that the window 62 faces downwardly towards the pill drop door 46 of the respective cartridge slot 42.

Figure 14:
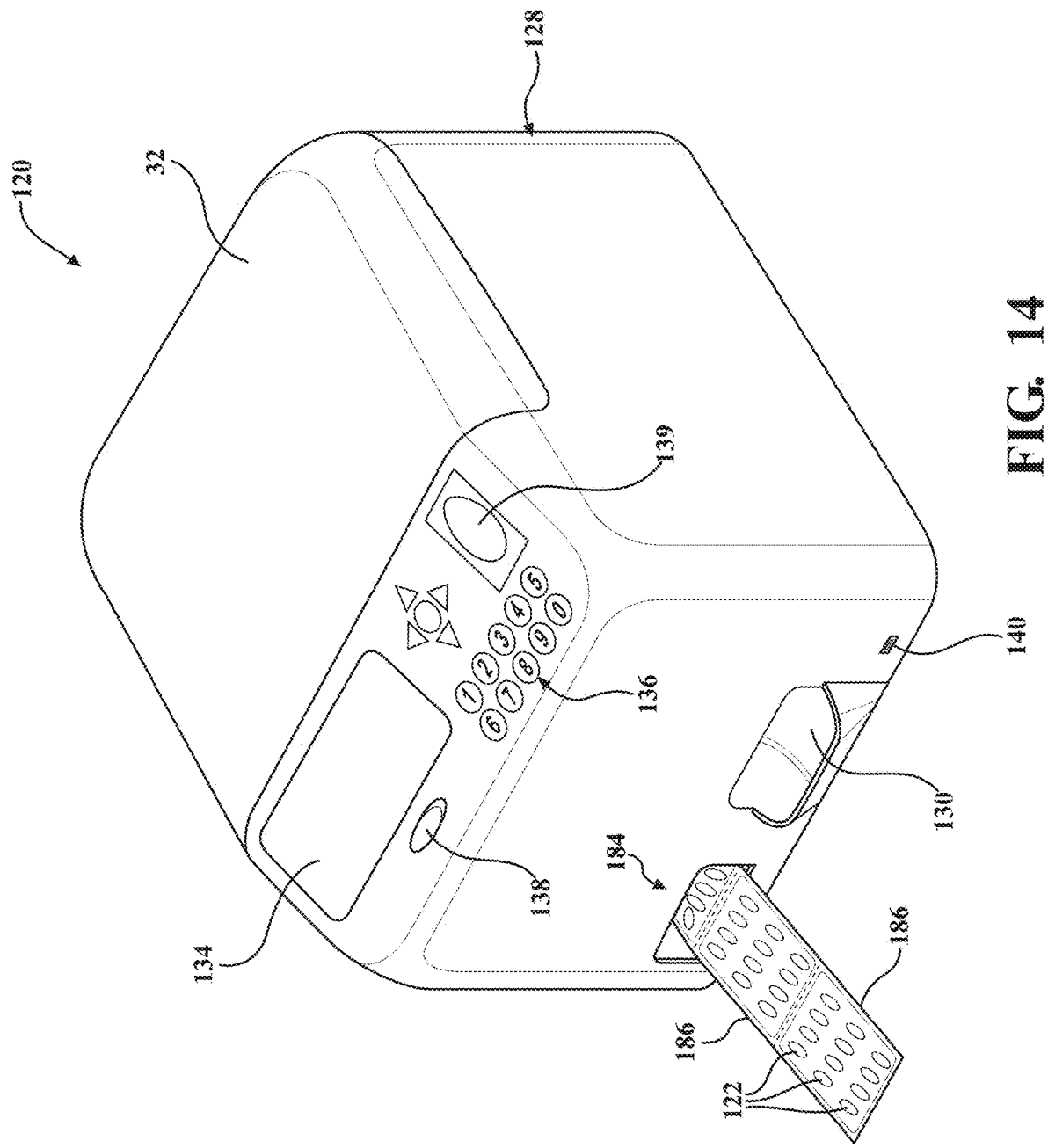
FIG. 14 is a perspective elevation view of a second exemplary embodiment of the medication dispensing device.

Referring now to FIG. 14, an alternate embodiment of the dispensing device 120 is generally shown with like numerals, separated by a prefix of "1" identifying corresponding parts with the parts described above. In this embodiment, the dispensing device 120 further includes a pouch dispensing system 184 that is configured to automatically guide the pills 122 from cartridges contained in the interior of the housing 128 into individual pouches 186 that can be removed from the dispensing device 120 and taken with the user they take carry their medications while away from the dispensing device 120. This may be helpful for users whose medication schedules require them to take doses at times when they are not at home. The pouch dispensing system 184 may dispense any desired number of doses in separate pouches or packages 186. Thus, the user can individually package enough doses of medication to take with them for an extended period, e.g., a week-long vacation. The dispensing device 120 may include a switching device, which may include one or more gates, that can be configured to direct the pills 22 to either the dispensing tray 130 or the pouch dispensing system 184.

In an example embodiment, the pouch dispensing system 184 includes a reel of refillable plastic or polymeric film. The pouch dispensing system can fold the film to form first and second opposing body panels and then join the body panels together with a plurality of spaced apart first seals (such as seals formed through a heat sealing operation) that extend perpendicularly to the fold to form a plurality of pockets that the pills 122 can be inserted into. The pouch dispensing system 184 automatically inserts the pills 122 into the pockets and then forms a second seal that extends between adjacent ones of the first seals to capture the pills 122 in the pockets. The first seals may then be perforated to allow the pockets to be broken apart into individual flexible packages 186 containing the pills 122 therein. In some embodiments, the pockets can be automatically cut apart from one another to form the individual flexible packages 186.

Figure 15:
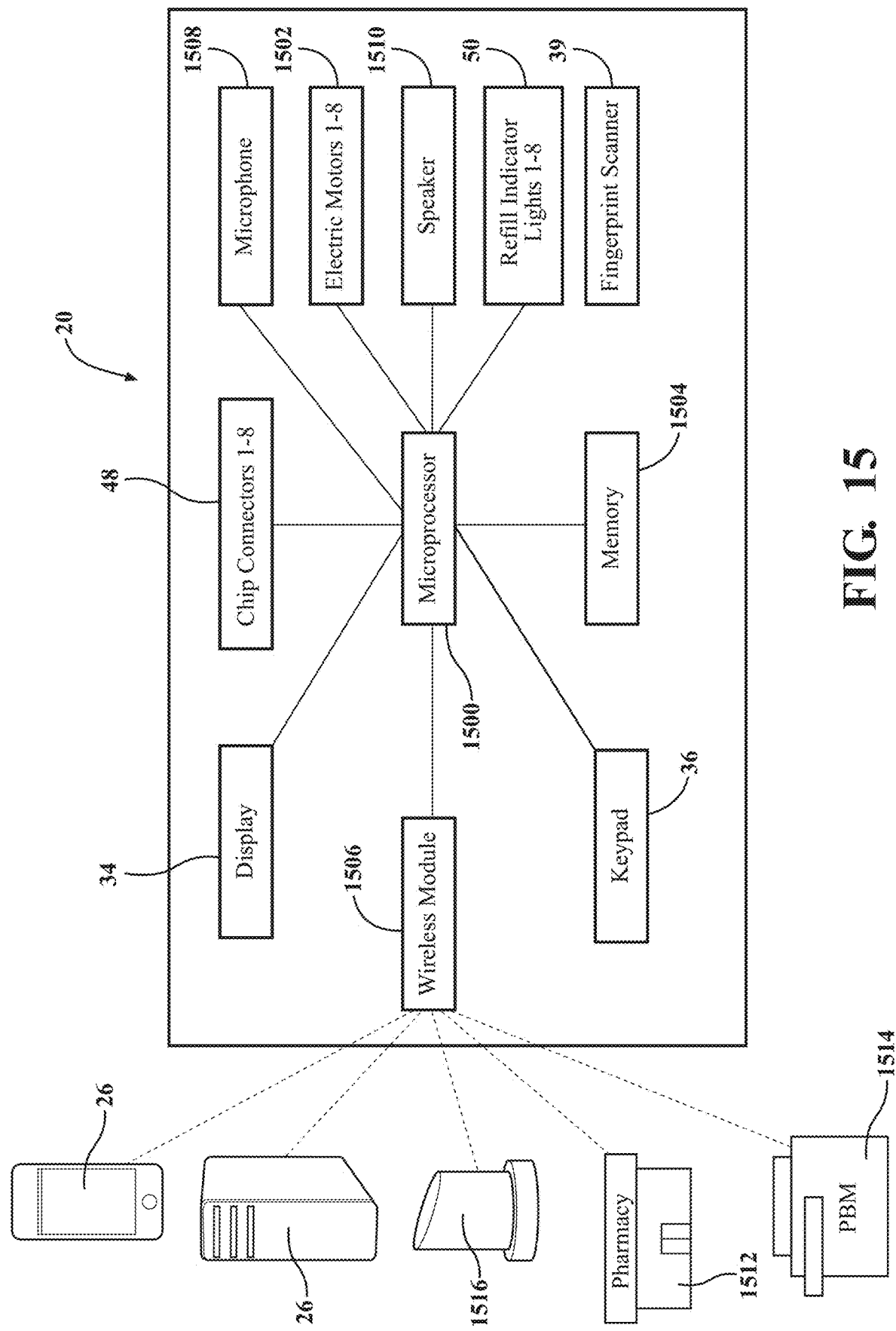
FIG. 15 is a schematic view showing many of the electrical components of the dispensing device.

Referring now to FIG. 15, the electrical system of the dispensing device 20 is schematically illustrated. As shown, the dispensing device 20 includes a processor 1500, such as a microprocessor, that is in electrical communication with a memory 1504 so that it can read from and write to the memory 1504. The processor 1500 may include any suitable number or types of processors. The memory 1504 is preferably of the non-volatile type such that the data stored thereon is not lost in the event of a power failure in the dispensing device 20. The memory 1504 may comprise a single disk or a plurality of disks (e.g., hard drives) and includes a storage management module that manages one or more partitions within the memory 1504. In some embodiments, the memory 1504 may include flash memory, semiconductor (solid state) memory or the like. The memory 1504 may include Random Access Memory (RAM), Read-Only Memory (ROM), or a combination thereof. The memory 1504 may include instructions that, when executed by the processor 1500, cause the processor 1500 to, at least, control various aspects of the dispensing device 20.

The memory 1504 contains data that includes: (1) which medications are contained in the cartridges 24 presently found in the cartridge slots 42; (2) the medication counts in those cartridges 42; (3) an automatic dispensing schedule (that can be adjusted by the user, a pharmacy 1512, or a pharmacy benefit manager 1514; and (4) a log containing time stamps of all dispensing events. The data contained in the memory 1504 is continuously updated by the processor 1500 when appropriate.

The microprocessor 1500 is also in electrical communication with the chip readers 48, thereby allowing the processor 1500 to receive and process the data contained on the chips 49 of the cartridges 24 in the cartridge slots 42. The microprocessor 1500 is also in electrical communication with the electric motors 1502 so that it can activate and deactivate the electric motors 1502 to dispense pills 22 from the cartridges 24 in the manner described above in response to either an automatic pill dispensing schedule or a manual request. The microprocessor 1500 is further in electrical communication with the refill indicator lights 50 to activate the appropriate refill indicator light(s) 50 if the microprocessor 1500 determines that the medication count in any of the cartridges 24 falls below the predetermined threshold.

The dispensing device 20 further includes a wireless module 1506 that is configured to transmit and receive data with the external device 26, with the pharmacy 1512, with the pharmacy benefit manager 1514, with a voice assistant 1516, or with any other suitable device. The wireless module 1506 could be configured to communicate with any of these devices via one or more of Bluetooth®, wireless fidelity (WiFI®), near field communications (NFC®), cellular communication, or any suitable wireless protocol or protocols or combination thereof. Thus, through the wireless module 1506, the automatic dispensing schedule can be downloaded and/or updated remotely, by the user or the user's medical provider, and the medication count and dispensing log data can be uploaded to and accessed through the external device 26 by either the user or a medical provider.

The dispensing device 20 may also be provided with a security system, which must be cleared prior to dispensing one or more types of pills 22 contained therein. The security system relies on a positive identification of the user. In the exemplary embodiment of FIG. 1, the user's identification is verified using the fingerprint scanner 39 on the housing 28. In other embodiments, the user's identification is verified using, for example, a personal identification number (PIN), facial recognition, a mobile phone app, a card reader, a Universal Serial Bus (USB) token, a Rivest-Shamir-Adleman (RSA) token, etc. The security system can also utilize one or more sensors in a user's mobile device, such as the external device 26, to establish the positive identification. That is, before a medication is dispensed, the dispensing device 20 can communicate with the external device 26 which, in turn, will require the user to verify the user's identity through, for example, a fingerprint sensor or a facial identification sensor built into the external device 26.

In some embodiments, the dispensing device 20 may include an input device, such as a microphone 1508, that is configured to receive audible signals and an output device, such as a speaker 1510, that is configured to output audible signals. The audible signals may include voice commands from the user (e.g., or caretaker and the like), an audible indication from a mobile computing device (e.g., a wearable device, a smart phone, and the like), any other suitable audible signal, or a combination thereof. For example, the user may provide voice commands directly to the dispensing device 20 using the input device and receive feedback through an output device.

Additionally, or alternatively, the user may utilize the external device 26 to provide audible reminders through a speaker 1510 for taking various medications. The external device 26 may generate an audible reminder at a predetermined time (e.g. corresponding to a time to take a particular mediation). The input device may receive the audible signal. The dispensing device 20 may dispense medication corresponding to the audible signal. The external device 26 may run instructions stored therein to operate an application that works with the dispensing device 20. The drug regimen reminders can also be output by the external device 26 based on the dosage schedule information that the dispensing device 20 knows from scanning the chip (or otherwise reading the data) on the cartridge 24. The user of the dispensing device 20 can opt-in to receiving notifications or reminders that are generated by the dispensing device 20 and communicated to the external device 26 associated with the user. In an example embodiment, the user's external device 26 is authorized by interaction with the pharmacy benefit manager 1514 or an insurance computing system, which can authorize use of the dispensing device 20 and gathering information from the dispensing device 20.

Figure 16:
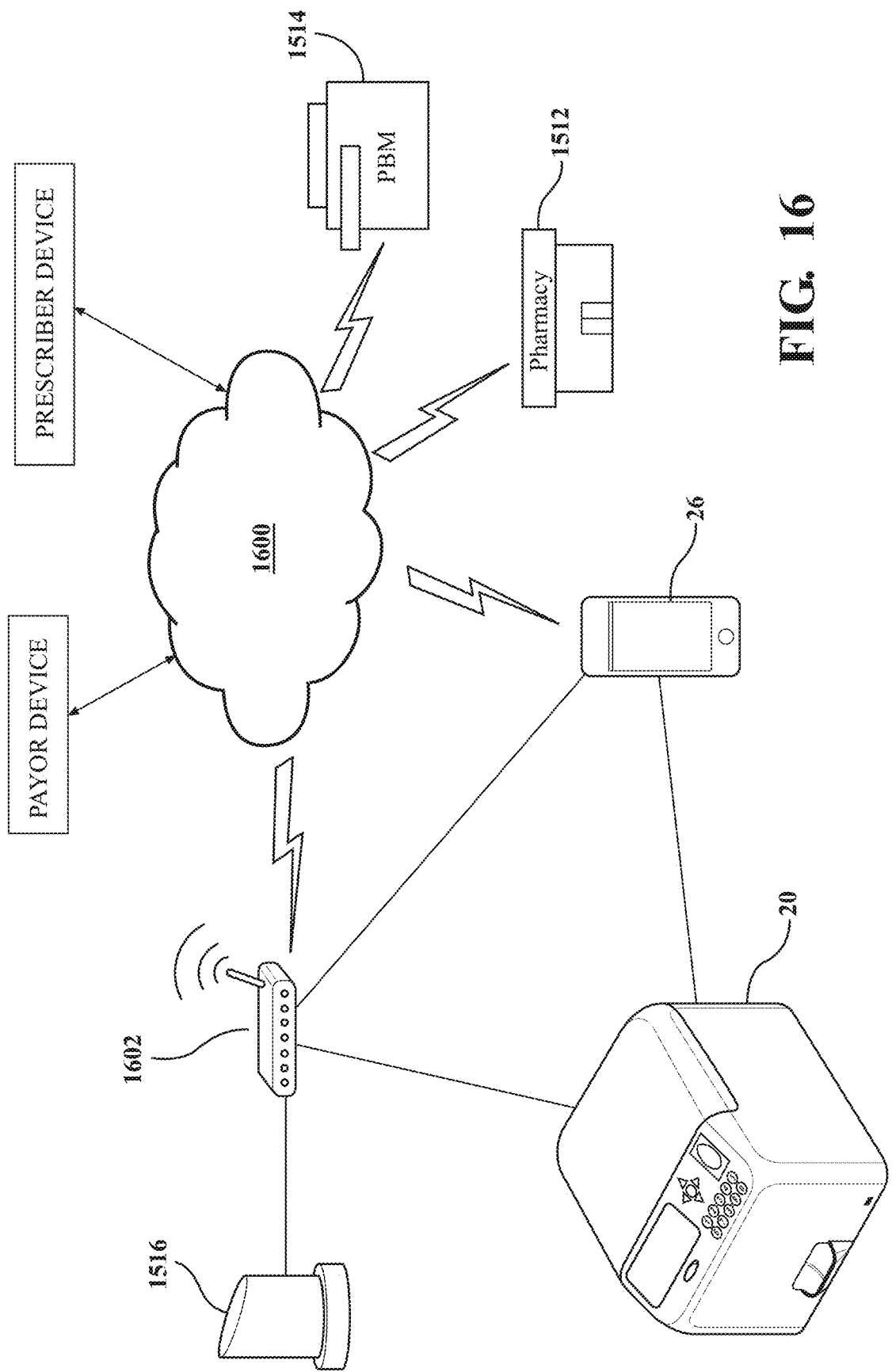
FIG. 16 is a schematic view showing an environment in which the dispensing device operates.

FIG. 16 is a schematic view showing an eco-system in which the dispensing device 20 can operate. The dispensing device 20 is in electrical communication with the internet 1600 via a portal, such as a router 1602 (wired or wireless) or the external device 26 or through any suitable internet gateway. Through the internet 1600, the dispensing device 20 is able to communicate with the pharmacy 1512 and with the pharmacy benefit manager 1514, thereby allowing the pharmacy 1512 and the pharmacy benefit manager 1514 to monitor the dispensing of pills 22 out of the dispensing device 20. Thus, the pharmacy 1512 and/or pharmacy benefit manager 1514 are able to remotel monitor a user's compliance to their medication schedule without any direct interaction with the user. In some embodiments, the pharmacy 1512 and/or the pharmacy benefit manager 1514 can automatically order a new cartridge 24 in response to the quantity of that medication in the dispensing device 20 falling below a predetermined threshold. The dispensing device 20 can also communicate with the external device 24 or with the voice assistant 1516 (such as those sold by Google®, Amazon®, and Apple®) directly and/or via the router 1602.

The dispensing device 20 may use its communication features, e.g., audio, VOIP, or text, to call a pharmacist device. When this communication is established, the dispensing device may encrypt the communication to ensure private communication. Such a communication can address medication concerns or questions. The communication functions can include the display screen 34 and a microphone and/or speaker built into the dispensing device 20. Each of these components can be controlled by control circuitry and use transmission circuitry to communicate with remote devices. In an example embodiment, the display device 20 may use its display screen 34 to show video of a pharmacist (or nurse) speaking in real-time for a more personal interaction with the user.

Additional devices may communicate with parties in the communication system. The additional devices can be, for example, a payer device or a prescriber device. The payer device can be part of an adjudication system or an insurance company system. The prescriber device may be part of a medical care facility or an individual medical care provider computing system, may be the prescriber of the medication and the payer (such as an insurance company). These additional devices may be directly connected or indirectly connected in which case the pharmacy benefit manager 1514 or pharmacy 1512 could be an intermediary to the payer or prescriber devices.

The user of the dispensing device 20 may interact with the external device 26 to provide various voice or non-voice commands. The commands may indicate a user's desire to refill a prescription, dispense daily medications, dispense periodic medications, or other suitable commands. The external device 26 may communicate with the dispensing device 20 to provide data corresponding to voice commands, and the dispensing device 20 may take action in response to receiving the data from the external device 26. For example, the dispensing device 20 may communicate with the pharmacy 1512 to refill a prescription based on data received from the external device 26. It should be understood that the dispensing device 20 may receive any suitable data from the external device 26 and may take any suitable action in response to the receipt of that data.

Figure 17:
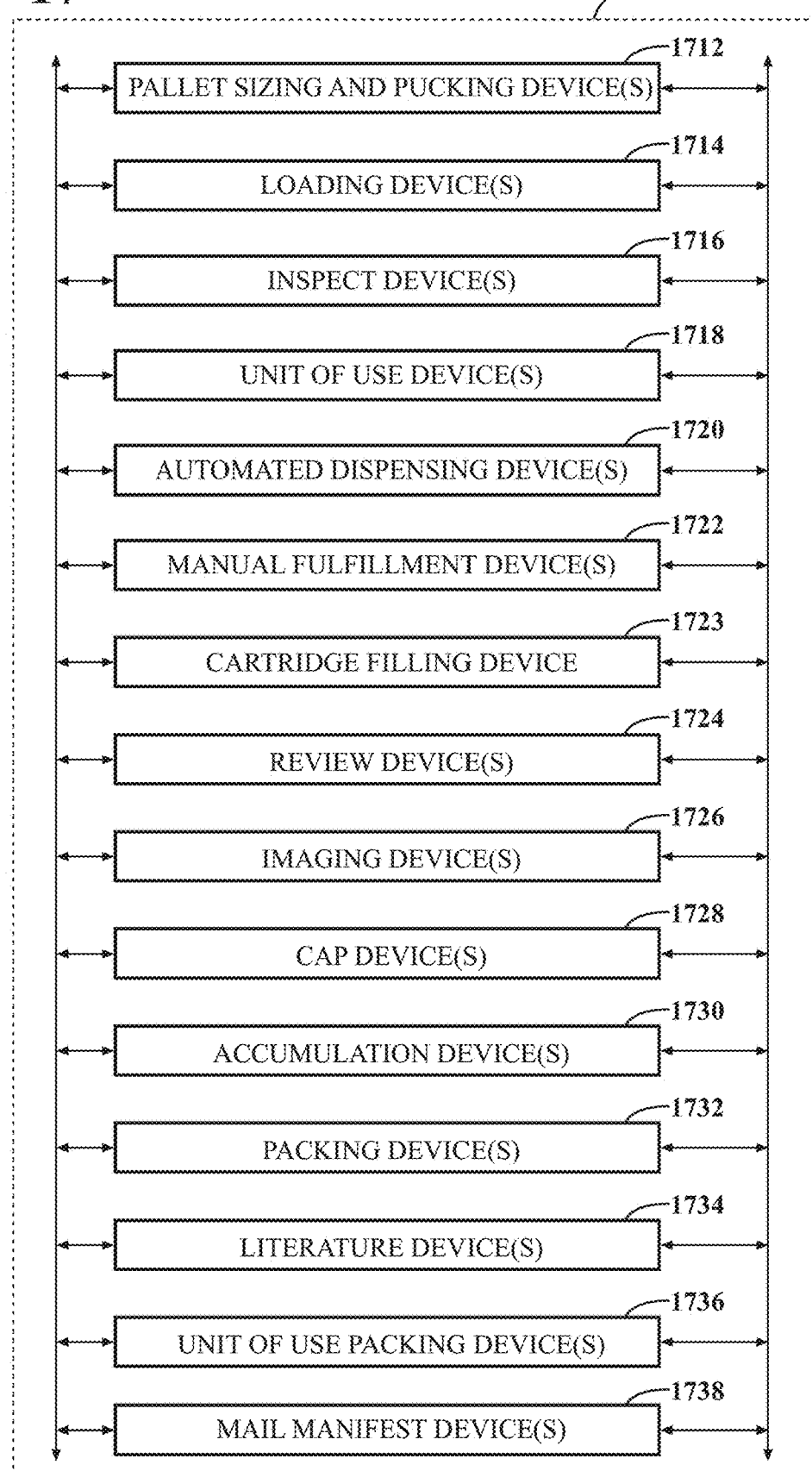
FIG. 17 is a schematic view showing an exemplary pharmacy that can fill cartridges for the medication dispensing device.

FIG. 17 generally illustrates the pharmacy 1512 according to the principles of an embodiment of the present disclosure. The pharmacy 1512 may be used to process and fulfill prescriptions and prescription orders. After fulfillment, the fulfilled prescriptions are packed for shipping. The dispensing device 20 may be used with other pharmacy systems and the like.

The pharmacy 1512 may include devices in communication with the pharmacy benefit manager 1514 order processing device, and/or the storage device, directly or over the network. Specifically, the pharmacy 1512 may include pallet sizing and pucking device(s) 1712; loading device(s) 1714; inspect device(s) 1716, unit of use device(s) 1718, automated dispensing device(s) 1720, manual fulfillment device(s) 1722 (which may be fulfill environmentally controlled drugs), cartridge filling device(s) 1723, review devices 1724, imaging device(s) 1726, cap device(s) 1728, accumulation devices 1730, packing device(s) 1732, literature device(s) 1734, unit of use packing device(s) 1736 (which may be pack environmentally controlled drugs), and mail manifest device(s) 1738. Further, the pharmacy 1704 may include additional devices, which may communicate with each other directly or over the network.

In some embodiments, operations performed by one of these devices 1712-1738 may be performed sequentially, or in parallel with the operations of another device as may be coordinated by the order processing device, which may include a dedicated processor in operable communication with a memory. In some embodiments, the order-processing device tracks a prescription with the pharmacy based on operations performed by one or more of the devices 1712-1738.

In some embodiments, the pharmacy may transport prescription drug containers, for example, among the devices 1712-1738 in the high-volume fulfillment center, by use of pallets. The pallet sizing and pucking device 1712 may configure pucks in a pallet. A pallet may be a transport structure for a number of prescription containers, and may include a number of cavities. A puck may be placed in one or more than one of the cavities in a pallet by the pallet sizing and pucking device 1712. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device based on prescriptions that the order processing device decides to launch. The arrangement logic may be implemented directly in the pallet sizing and pucking device 1712. Once a prescription is set to be launched, a puck suitable for the appropriate size of container for that prescription may be positioned in a pallet by a robotic arm or pickers. The pallet sizing and pucking device 1712 may launch a pallet once pucks have been configured in the pallet.

The loading device 1714 may load prescription containers into the pucks on a pallet by a robotic arm, a pick and place mechanism (also referred to as pickers), etc. In various embodiments, the loading device 1714 has robotic arms or pickers to grasp a prescription container and move it to and from a pallet or a puck. The loading device 1714 may also print a label that is appropriate for a container that is to be loaded onto the pallet, and apply the label to the container. The pallet may be located on a conveyor assembly during these operations (e.g., at the high-volume fulfillment center, etc.).

The inspect device 1716 may verify that containers in a pallet are correctly labeled and in the correct spot on the pallet. The inspect device 1716 may scan the label on one or more containers on the pallet. Labels of containers may be scanned or imaged in full or in part by the inspect device 1716. Such imaging may occur after the container has been lifted out of corresponding puck by a robotic arm, picker, etc., or may be otherwise scanned or imaged while retained in the puck. In some embodiments, images and/or video captured by the inspect device 1716 may be stored in the storage device as order data.

The unit of use device 1718 may temporarily store, monitor, label, and/or dispense unit of use products. In general, unit of use products are prescription drug products that may be delivered to a user or member without being repackaged at the pharmacy 1704. These products may include pills in a container, pills in a blister pack, inhalers, temperature-controlled drugs, etc. Prescription drug products dispensed by the unit of use device 1718 may be packaged individually or collectively for shipping, or may be shipped in combination with other prescription drugs dispensed by other devices in the high-volume fulfillment center.

At least some of the operations of the devices 1712-1738 may be directed by the order processing device. For example, the manual fulfillment device 1722, the review device 1724, the automated dispensing device 1720, and/or the packing device 1732, etc. may receive instructions provided by the order processing device.

The automated dispensing device 1720 may include one or more devices that dispense prescription drugs or pharmaceuticals into prescription containers in accordance with one or multiple prescription orders. In general, the automated dispensing device 1720 may include mechanical and electronic components with, in some embodiments, software and/or logic to facilitate pharmaceutical dispensing that would otherwise be performed in a manual fashion by a pharmacist and/or pharmacist technician. For example, the automated dispensing device 1720 may include high-volume fillers that fill a number of prescription drug types at a rapid rate and blister pack machines that dispense and pack drugs into a blister pack. Prescription drugs dispensed by the automated dispensing devices 1720 may be packaged individually or collectively for shipping, or may be shipped in combination with other prescription drugs dispensed by other devices in the high-volume fulfillment center.

The manual fulfillment device 1722 controls how prescriptions are manually fulfilled. For example, the manual fulfillment device 1722 may receive or obtain a container and enable fulfillment of the container by a pharmacist or pharmacy technician. In some embodiments, the manual fulfillment device 1722 provides the filled container to another device in the pharmacy fulfillment devices to be joined with other containers in a prescription order for a user or member. For example, non-environmentally controlled drugs and environmentally controlled drugs may be filled and joined together for packaging.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. or retrieve drugs from a cooler. Some portions of the manual fulfillment process may be automated by use of a machine. For example, counting of capsules, tablets, or pills may be at least partially automated (such as through use of a pill counter). Prescription drugs dispensed by the manual fulfillment device 1722 may be packaged individually or collectively for shipping, or may be shipped in combination with other prescription drugs dispensed by other devices in the high-volume fulfillment center.

Figure 11:
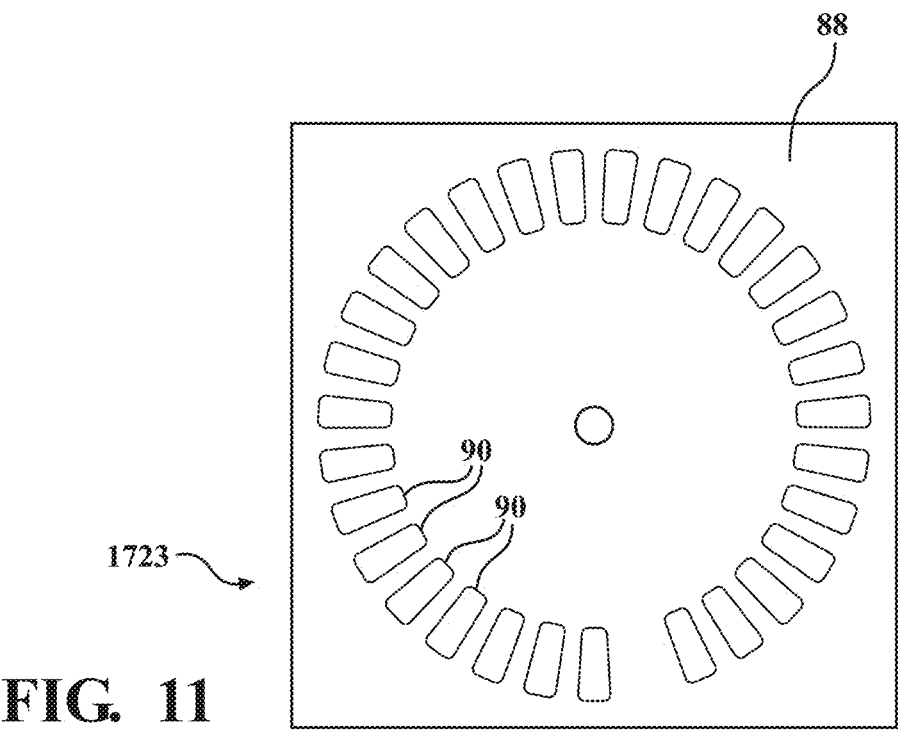
FIG. 11 is a top elevation view of an exemplary embodiment of a fill plate.

The cartridge filling device 1723 is adapted to automatically fill and package cartridges 24 for the dispensing device 20 and is shown in FIGS. 11 and 12. The cartridge filling device 1723 includes a fill plate 88 with a plurality of circumferentially spaced apart through openings 90 that are arranged in a pattern that is similar to the pattern of the pill chambers 76 of the rotational wheel 56. The fill plate 88 preferably includes the exact number of openings 90 as pills 22 are to go into a cartridge 24, and those openings 90 are preferably shaped to hold no more than one pill 22 each. A gate 92 is disposed below the fill plate 88 and is movable between a closed position (shown in FIG. 11) and an open position (shown in FIG. 12). When in the closed position, the gate 92 closes the through openings 90 so that pills 22 can stay in the openings 90 until the gate 92 is opened.

To fill a cartridge 24, an empty rotational wheel 56 is positioned below the gate 92, and the openings 90 are filled with pills 22. The gate 92, thereby allowing the pills 22 to fall into the respective pill chambers 76 of the rotational wheel 56. A cap may then be affixed with the cartridge 24 to retain the pills inside of the rotational wheel 56. The cartridge filling device 1723 may be automated to expedite the filling operation. Cartridges 24 may be refilled with the cartridge filling device 1723 after the medication contained in them has been depleted, i.e., the cartridges 24 are recyclable.

The review device 1724 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 1724 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review may be performed at a manual review station.

The imaging device 1726 may image containers once they have been filled with pharmaceuticals. The imaging device 1726 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. A temperature-controlled package may be imaged to ensure the correct coolant is in the package. The images may be transmitted to the order processing device and/or stored in the storage device as part of the order data.

The cap device 1728 may be used to cap or otherwise seal a prescription container. In some embodiments, the cap device 1728 may secure a prescription container with a type of cap in accordance with a user preference (e.g., a preference regarding child resistance, etc.), a plan sponsor preference, a prescriber preference, etc. The cap device 1728 may also etch a message into the cap, although this process may be performed by a subsequent device in the high-volume fulfillment center.

The accumulation device 1730 accumulates various containers of prescription drugs in a prescription order. The accumulation device 1730 may accumulate prescription containers from various devices or areas of the pharmacy. For example, the accumulation device 1730 may accumulate prescription containers from the unit of use device 1718, the automated dispensing device 1120, the manual fulfillment device 1722, and the review device 1724. The accumulation device 1730 may be used to group the prescription containers prior to shipment to the member.

The literature device 1734 prints, or otherwise generates, literature to include with each prescription drug order. The literature may be printed on multiple sheets of substrates, such as paper, coated paper, printable polymers, or combinations of the above substrates. The literature printed by the literature device 1734 may include information required to accompany the prescription drugs included in a prescription order, other information related to prescription drugs in the order, financial information associated with the order (for example, an invoice or an account statement), etc.

In some embodiments, the literature device 1734 folds or otherwise prepares the literature for inclusion with a prescription drug order (e.g., in a shipping container). In other embodiments, the literature device 1734 prints the literature and is separate from another device that prepares the printed literature for inclusion with a prescription order.

The packing device 1732 packages the prescription order in preparation for shipping the order. The packing device 1732 may box, bag, or otherwise package the fulfilled prescription order for delivery. The packing device 1732 may further place inserts (e.g., literature or other papers, etc.) into the packaging received from the literature device 1734. For example, bulk prescription orders may be shipped in a box, while other prescription orders may be shipped in a bag, which may be a wrap seal bag.

The packing device 1732 may label the box or bag with an address and a recipient's name. The label may be printed and affixed to the bag or box, be printed directly onto the bag or box, or otherwise associated with the bag or box. The packing device 1732 may sort the box or bag for mailing in an efficient manner (e.g., sort by delivery address, etc.). The packing device 1732 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise to a delivery location. Some packages will be delivered using autonomous delivery vehicles, e.g., ground vehicles or aircraft, to the delivery location.

The unit of use packing device 1736 packages a unit of use prescription order in preparation for shipping the order. The unit of use packing device 1736 may include manual scanning of containers to be bagged for shipping to verify each container in the order. In an example implementation, the manual scanning may be performed at a manual scanning station. A mail manifest device 1738 may print mailing labels used by the packing device 1732 and may print shipping manifests and packing lists.

Multiple devices may share processing and/or memory resources. The devices 1712-1738 may be located in the same area or in different locations. For example, the devices 1712-1738 may be located in a building or set of adjoining buildings. The devices 1712-1738 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

The dispensing device 20 may also contain medications for multiple users, e.g., different members of a family. In use, the dispensing device 20 may validate which user is interacting with the dispensing device 20 through a number of different means. For example, in some embodiments, the security system of the dispensing device 20 can validate which user is interacting with the dispensing device 20 using a positive identification means. In other embodiments, the user can be validated by selecting a user profile and entering a passcode or password on the display screen 34 or through a positive voice identification either through the microphone 1508 or through the voice assistant 1516. The processor 1500 may also be configured to verify the identity of the user using various biometric data, such as a facial scan, a retina scan, a fingerprint scan, or the like. For example, the processor 1500 may receive or retrieve a file that contains the facial recognition data and compare it to the image data captured by an image capturing device. The image capturing device may include a camera that is disposed on the dispensing device 20 or may be associated with the external device 26 or any suitable image capturing device. The processor 1500 may compare the facial recognition data with the image data using facial recognition software. The processor 1500 may verify the user's identity in response to a determination that the facial recognition data matches the image data.

The processor 1500 may also compare an audible input to a corresponding stored file (e.g., a similar audible input, such as a sample speech of the user, a corresponding tone, or other suitable audible data) to verify the identity of the user based on a determination that the audible input matches the corresponding file.

The fingerprint scan can either be from the fingerprint scanner 39 on the housing 28 for from the external device 26. The processor 1500 may verify the identity of the user by comparing the fingerprint scan with stored fingerprints associated with the user.

In some embodiments, the processor 1500 may process a retina scan that may be taken by a retina scanner on the dispensing device 20 or on the external device 26 or any suitable device. The processor 1500 may compare the retina scan with stored retina scans corresponding to the user and verify the identity of the user in response to a determination that the received retina scan matches the stored retina scans corresponding to the user.

In some embodiments, the dispensing device 20 may be configured to scan a quick response (QR) code or barcode that is associated with the user. For example, the user may receive a WR code or a barcode from the application, an SMS message, a text message, an email, a phone call, or other suitable QR code source. The user may print the QR code or barcode or may present the QR code or the barcode to the external device 26. The processor 1200 may scan, using an image capturing device on the dispensing device 20 or the external device 26, the QR code or the barcode. The processor 1500 may compare the scanned QR code and/or barcode to WR code and/or barcode stored on the memory 1504 or other suitable location. The QR code and/or barcode stored on the memory 1504 or other suitable location may be generated by the processor 1500. For example, the processor 1500 may generate the QR code and/or barcode stored on the memory 1504 or other suitable location and the QR code and/or barcode received by the user. In some embodiments, the processor 1500 may receive the QR code and/or barcode from the pharmacy application. The processor 1500 may verify the identity of the user in response to the QR code and/or barcode presented by the user matching the QR code and/or barcode stored on the memory 1504 or other suitable location.

In some embodiments, the processor 1500 may receive a numeric value from the user (e.g., via a keypad 36 input, a display screen 34 input, or another suitable input device). For example, the user may receive a numeric value from the pharmacy application on the external device 26. The user may then provide or input the numeric value to the dispensing device 20. The processor 1500 may verify the identity of the user based on a comparison of the numeric value to a numeric value communicated to the processor 1500 via the pharmacy application. It should be understood that the processor 1500 may receive any other suitable information from the user in addition to or instead of those described herein that the processor 1500 may use to verify the identity of the user.

In some embodiments, the dispensing device 20 may include one or more sensors configured to measure or sense various aspects of the dispensing device 20 and/or an environment external to the dispensing device 20. For example, the dispensing device 20 may include a motion sensor or other suitable sensor(s) configured to detect motion proximate to the dispensing device. The processor 1500 may receive data from the sensor and may illuminate a light associated with the dispensing tray 30 in response to the detected motion.

In some embodiments, the dispensing device 20 may include one or more vital measurement devices. For example, the dispensing device 20 may include a pulse monitor, a blood pressure cuff (e.g., of another suitable blood pressure measuring device), other suitable vital measurement devices, or a combination thereof. The user may interact with the one or more vital measurement devices. For example, the user may use a pulse monitor to measure the user's pulse. The processor 1500 may receive a pulse measurement from the pulse monitor indicating the user's pulse. The processor 1500 may store the pulse measurement in a user measurement table database along with any other user measurements data. The user measurements data may be stored on the memory 1504, on a cloud computing device, on a mobile computing device of the user, and/or another suitable location. For example, the processor 1500 may store and/or update the user measurements data in the memory 1504.

In some embodiments, the user may interact with a blood pressure measuring device of the dispensing device 20. The user may use the blood pressure measuring device to measure a blood pressure of the user. The processor 1500 may receive a blood pressure measurement from the blood pressure measuring device indicating the blood pressure of the user. The processor 1500 may update the user measurements data to include the blood pressure measurement.

In some embodiments, the user may interact with a thermometer of the dispensing device 20. The user may use the thermometer to measure a temperature of the user. The processor 1500 may receive a temperature measurement from the thermometer indicating the user's temperature. The processor 1500 may update the user measurement data to include the temperature measurement. It should be understood that the dispensing device 20 may include any suitable measuring device that the user may interact with to provide measurement data corresponding to the user.

In some embodiments, the user may interact with a keyboard, touch screen, or other suitable input device to provide various measurements (e.g., pulse measurement, blood pressure measurement, temperature measurement, insulin measurement, other suitable measurements, or a combination thereof). For example, the user may interact with a touch screen on the dispensing device 20 to provide various measurements to the dispensing device 20. In some embodiments, the user may interact with an application on a corresponding mobile computing device, such as the external device 26. The user may provide user measurement data using the application. The application may communicate the user measurement data, using the mobile computing device, to the dispensing device 20. The processor 1200 may store and/or update the user measurement data based on the received various measurements.

In some embodiments, the processor 1500 may be configured to communicate the user measurement data to a pharmacist and/or medical provider. The pharmacist and/or medical provider may review the user measurement data and determine whether to adjust one or more medication doses taken by the user. The pharmacist and/or medical provider may, using a suitable computing device, communicate an adjusted medication dose to the dispensing device 20. The dispensing device 20 may adjust a dispensing amount for the medication based on the adjusted dose for the medication.

In some embodiments, the processor 1500 using the wireless module 1506, may identify other devices on the network. For example, the processor 1500 may identify devices on the network operating according to the same communications protocol. The other devices may include Internet of Things (IoT) enabled devices, such as a coffee maker, a refrigerator, a smart switch, a smart light, an alarm clock, other suitable devices, or a combination thereof. The processor 1500 may identify behavioral patterns of the user based on communications with the other devices on the network. For example, the user may start a coffee maker, open a refrigerator, turn on one or more lights, turn off an alarm clock, and the like.

The processor 1500 may adjust a dispensing schedule of medications in the dispensing device 20 based on an identified behavioral pattern. For example, the dispensing device 20 may dispense medications in the dispensing device 20 to the dispensing tray 30 at a time that corresponds to the user being within a range of the dispensing device 20. The processor 1500 may identify the time that corresponds to the user being within the range of the dispensing device 20 based on the identified behavioral pattern.

In some embodiments, the processor 1500 may determine whether various medications dispensed by the dispensing device 20 and consumed by the user have adverse effects on the user. For example, the processor 1500 may identify a sudden change in the behavioral pattern of the user and determine that one or more medications may be contributing to the change in behavioral patterns. For example, the processor 1500 may be in communication with a machine learning mechanism configured to identify behavioral changes corresponding to potential side effects of certain medications. The processor 1500 may generate an indication (e.g., such as a message or other suitable indication) indicating that the user may be experiencing side effects from one or more medications. The processor 1500 may communicate, using the router 1602, the indication to the pharmacist and/or medical provider. The pharmacist and/or medical provider may contact the user and/or may adjust one or more doses of medications being consumed by the user.

In some embodiments, the dispensing device 20 may dispense a multiple day supply of medications in response to a request by the user. For example, the user may provide an input using any suitable input described herein, to the dispensing device 20 indicating that the user may be away from the dispensing device 20 for a period (e.g., on vacation, on a work trip, in the hospital, or any other suitable reason). For example, the user may be taking a trip and will not be near the dispensing device 20 for the period. The user may provide the dispensing device 20 with a number of days that the user will be away from the dispensing device 20. The processor 1500 may receive the number of days and determine a quantity of each of the various medications taken by the user for the number of days. The processor 1500 may dispense the quantity of each of the various medications. In some embodiment, the processor 1500 may communicate with a pharmacist and/or medical provider indicating that the user has requested the multiple day supply of medication. The pharmacist and/or medical provider may determine whether to allow the dispensing device 20 to dispense the multiple day supply, the processor 1500 may receive an indication from the pharmacists and/or medical provider instructing the dispensing device 20 to dispense the multiple day supply. In response to the processor 1500 receiving instructions from the pharmacist and/or medical provider indicating not to dispense the multiple day supply, the processor 1500 may provide to the user (e.g., via the touch screen, communication via the mobile device, or any suitable mechanism), a notification indicating to the user to contact the pharmacist and/or medical provider.

In some embodiments, the processor 1500 may be configured to communicate a calendaring application associated with the user. For example, the user may utilize a calendaring application on the external device 26 or any suitable computing device. The processor 1500 may identify travel plans stored in the calendaring application indicating that the user may be away from the dispensing device 20 for a period. The processor 1500 may generate a request to a pharmacist and/or medical provider indicating that the user may be away from the dispensing device 20. The request may be for the pharmacist and/or medical provider to contact the user. In some embodiments, the processor 1500 may dispense a multiple day supply in response to identifying travel plans in the user's calendaring application.

In some embodiments, the processor 1500 may identify scheduled events in the calendaring application. For example, the processor 1500 may identify scheduled events that begin prior to a normal dispensing time. The processor 1500 may determine to dispense the medications to the dispensing tray 30 prior to the identified scheduled event (e.g., such that the user does not leave the proximity of the dispensing device 20 prior to the medications being dispensed).

In some embodiments, the processor 1500 may be configured to perform the methods described as follows. In some embodiments, the processor may communicate with various other devices such as mobile computing devices, networks, cloud computing devices, remotely located servers, and the like to perform the methods described herein.

As discussed above, the dispensing device 20 can either be operated automatically according to a preset schedule or the operation can be unscheduled. For automatic operation, a medication dispending schedule may be stored on the memory 1504 from the external device 26 (which could be controlled by either the user, a pharmacy, or a medical provider), from the keypad 36, or from the data contained on the chips 49 of the cartridges 24. The medication dispensing schedule may also be changed through any of these means when appropriate. When an automatic dispensing of a medication dose occurs, the dispensing device 20 preferably notifies the user of the event. The notification could be, for example, an audible noise played from the speaker 1510, a notification shown on the display screen 34, or a notification sent to the external device 26. Unscheduled dispensing of the pills 22 can be activated either through the external device 26 or by pressing the dispense button 38.

Once a dispensing command has been received, the processor 1500 instructs the electric motor 1502 associated with the cartridge 24 containing the dosage that was requested to rotate the incremental gear 44. As discussed above, this action has the effect of rotating the rotational wheel 56 about the central axis to expose the next sequential one of the pill chambers 76 to the pill drop door 46 of the stationary hub 54, i.e., the rotational wheel 56 is incremented from one pill chamber 76 to the next. The pill(s) 22 contained within the now-aligned pill chamber 76 then automatically fall out of the cartridge 24 and into the dispensing chute 51, which guides it to the dispensing tray 30. The fine pitch pattern of the gear teeth on the rotational wheel 56 allows for very precise advancement of the rotational wheel 56 to prevent any pills 22 contained in the now exposed pill chamber 76 from getting stuck and remaining in the pill chamber 76.

The processor 1500 then processes a notification to the user that the medication dose has been dispensed and records the dispensing event in the memory 1504. The dispensing event may also be uploaded to a remote location, such as a medical care provider or the external device 26 using the wireless module 1506. Next, the processor 1500 makes an appropriate adjustment to the medication count associated with the cartridge 24 that was just dispensed from in the memory 1504. If the new medication count has fallen below a predetermined threshold, then the processor 1500 activates the refill indicator light 50 associated with that cartridge 24. The processor 1500 may also automatically communicate with the pharmacy 1512 via the wireless module 1506 to automatically process the purchase of a new cartridge 24 to replace the nearly depleted cartridge 24.

The dispensing device 20 may also be programmed to dispense a plurality of doses simultaneously so that a user can put those doses into a separate pill container (not shown). This feature allows a user who is going to be leaving their home for an extended length of time to take their pills 22 with them without bringing along the dispensing device 22. The dispensing device 20 can be instructed to dispense multiple doses either from the external device 24 or through the keypad 30 or through any other input means. In the embodiment with the pouch dispensing system 184, the multiple doses may be contained in different pouches 186.

The dispensing device 20 may also be provided with a security system which must be cleared prior to dispensing of one or more types of medications contained therein. The security system relies on a positive identification of the user through one or more of a personal identification number (PIN), thumbprint, facial recognition, a mobile phone app, a card reader, a Universal Serial Bus (USB) token, a Rivest-Shamir-Adleman (RSA) token, etc. Each of the cartridges 24 is also preferably provided with a tamper-proof and/or child safety mechanism.

The dispensing device 20 can improve adherence to a therapy regime. The medication container can track the date and time of each medication dispensing event from a specific cartridge 24. The data from the dispensing device 20 can provide reminders to the user, e.g., through the external device or the display screen 34. The data from the dispensing device 20 can also be used to detect non-compliance, such as if the dispensing device 20 detects that a pill 22 is not removed from the dispensing tray 30, and communicate that non-compliance to assigned devices, which can be associated with a family member, a caregiver or a medical practitioner. The dispensing data from the medication container can also be used to identify medications characterized by poor adherence.

The dispensing device 20 can also include an interface that can alert the user to environmental conditions that may compromise the integrity of the medication (e.g., temperature sensors determining that ambient temperature has exceeded a certain temperature, that a thermal budget has been used, or that the interior a chamber has exceeded a moisture level. The circuitry in the dispensing device 20 through its communications circuitry can electronically communicate with prescribing doctor's devices, pharmacy devices, insurance companies, pharmacy benefits management devices, and other parties that may be interested in prescription practices and adherence.

Figure 18:
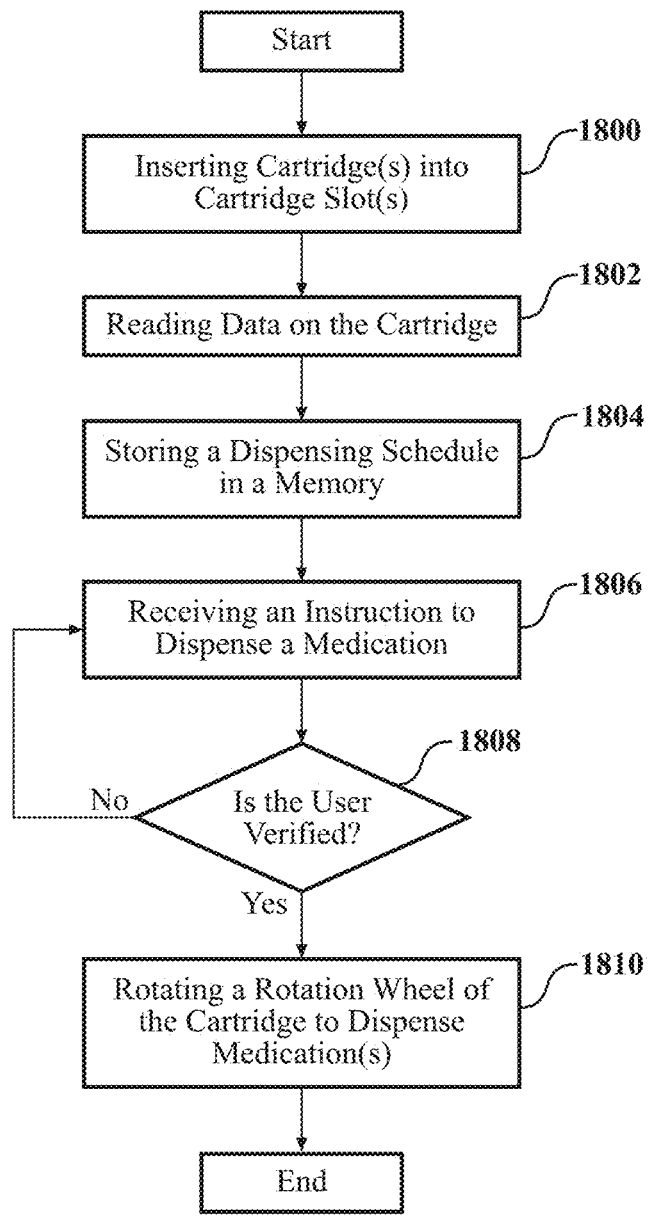
FIG. 18 is a flow chart illustrating an exemplary embodiment of a method of dispensing a medication to a user.

The flow chart set forth in FIG. 18 depicts an exemplary method of dispensing medications to a user. At step 1800, the method includes the step of inserting at least one cartridge 24 into at least one cartridge slot 42. At step 1802, the method proceeds with the step of reading data on the at least one cartridge 24 using the data reader 48. At step 1804, the method continues with the step 1804 of storing an automatic dispensing schedule in a memory 1504. In one embodiment, the automatic dispensing schedule is downloaded to the memory 1504 from the chip 49. The method proceeds with the step 1806 of receiving an instruction to dispense a medication. The instruction could come from either the automatic dispensing schedule or a demand. At decision step 1808, it is determined if a user's identification is verified. If the answer at step 1808 is no, then the method proceeds back to step 1806. If the answer at decision step 1810 is yes, then the method proceeds to step 1810. At step 1810, the method proceeds with rotating a rotational wheel of the cartridge 24 to dispense at least one medication from the at least one cartridge 1810.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or." That is, unless specified otherwise or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" throughout is not intended to mean the same embodiment or implementation unless described as such.

Implementations of the systems, algorithms, methods, instructions, etc., described herein may be realized in hardware, software, or any combination thereof. The hardware may include, for example, computers, intellectual property (IP) cores, application-specific integrated circuits (SICSs), programmable logic arrays, optical processors, programmable logic controllers, microcode, microcontrollers, servers, microprocessors, digital signal processors, or any other suitable circuit. In the claims, the term "processor" should be understood as encompassing any of the foregoing hardware, either singly or in combination. The terms "signal" and "data" are used interchangeably.

As used herein, the term "module" may include a packaged functional hardware unit designed for use with other components, a set of instructions executable by a controller (e.g., a processor executing software or firmware), processing circuitry configured to perform a particular function, and a self-contained hardware or software component that interfaces with a larger system. For example, a module may include an ASIC, a Field Programmable Gate Array (FPGA), a circuit, a digital logic circuit, an analog circuit, a combination of discrete circuits, gates, and other types of hardware or combinations thereof. In other embodiments, a module may include memory that stores instructions executable by a controller to implement a feature of the module.

Obviously, many modifications and variations of the present invention are possible in light of the above teachings and may be practiced otherwise than as specifically described while within the scope of the appended claims. Additionally, it is to be understood that all features of all claims and all embodiments can be combined with each other as long as they do not contradict each other.

What is claimed is:

1. A medication dispensing device, comprising:
a housing having an interior and including a plurality of cartridge slots, each of the cartridge slots including a drive mechanism;
a plurality of cartridges removably disposed in respective ones of the cartridge slots;
each cartridge including a stationary hub and a rotational wheel, the stationary hub having a window, the rotational wheel including a plurality of medication chambers containing medications, the rotational wheel being disposed in the stationary hub, the drive mechanism of the respective cartridge slot being operably connected with the rotational wheel and configured to rotate the rotational wheel relative to the stationary hub to selectively aligned the medication chambers with the window to dispense the medications contained in the medication chambers out of the cartridge;
each cartridge including a chip that includes data that is encrypted such that only the medication dispensing device associated with a desired user can read the data; and
the stationary hub of each cartridge having a non-circular tab that is located along a central axis about which the rotational wheel can rotate and that is received in a similarly shaped opening of the respective cartridge slot to orient the window in a vertically downward direction and to hold the window in the vertically downward direction as the rotational wheel rotates.

2. The medication dispensing device as set forth in claim 1 wherein the rotational wheel of each cartridge includes a plurality of teeth and wherein the drive mechanism of each cartridge slot includes an increment gear that is mechanically coupled with the teeth of the rotational wheel for driving rotation of rotational wheel relative to the stationary hub.

3. The medication dispensing device as set forth in claim 1 wherein the drive mechanism of each cartridge slot further includes an electric motor.

4. The medication dispensing device as set forth in claim 1 wherein each rotational wheel includes a plurality of radially extending walls that are circumferentially spaced apart from one another by the medication chambers.

5. The medication dispensing device as set forth in claim 1 further including a memory containing data related to an automatic dispensing schedule and a processor configured to control rotation of the increment gear to rotate the rotational wheel and dispense the medications from the cartridge according to the automatic dispensing schedule.

6. The medication dispensing device as set forth in claim 1 wherein the housing further includes a dispensing chute that guides the medications dispensed out of the cartridges through the windows to a dispensing tray.

7. The medication dispensing device as set forth in claim 1 further including a wireless module for communicating with an external device.

8. A medication dispensing device, comprising:
a housing having an interior and including a plurality of cartridge slots, each of the cartridge slots including a drive mechanism;
a plurality of cartridges removably disposed in the cartridge slots, each of the cartridges including a stationary hub and a rotational wheel, the rotational wheel being operably connected with the drive mechanism of the respective cartridge slot so that the rotational wheel can rotate about a central axis relative to the stationary hub, and the rotational wheel including a plurality of medication chambers that are circumferentially spaced apart from one another and that contain medications;
a processor configured to selectively and individually activate the drive mechanisms of the cartridge slots to selectively dispense medications out of any of the cartridges contained in the cartridge slots;
each cartridge including a chip that includes data that is encrypted such that only the medication dispensing device associated with a desired user can read the data; and
the stationary hub of each cartridge includes a non-circular tab that is located along a central axis about which the rotational wheel can rotate and that is received in a similarly shaped opening of the respective cartridge slot to orient a window of the stationary hub in a vertically downward direction and to hold the window in the vertically downward direction as the rotational wheel rotates.

9. The medication dispensing device as set forth in claim 8 wherein the processor is configured to dispense medications out of the cartridges according to either an automatic dispensing schedule or in response to a demand.

10. The medication dispensing device as set forth in claim 8 further including an identification verification system that is configured to only allow medications to be dispensed from the cartridges in response to a positive verification of a user.

11. The medication dispensing system as set forth in claim 10 wherein the identification verification system includes at least one sensor on either the dispensing device or an external device that is in electrical communication with the dispensing device.

12. The medication dispensing system as set forth in claim 11 wherein the at least one sensor is on the external device and wherein the external device is a cellular telephone.

13. The medication dispensing system as set forth in claim 12 wherein the at least one sensor on the external device is a fingerprint sensor or a facial identification sensor.

14. The medication dispensing system as set forth in claim 8 wherein the plurality of cartridges includes at least one cartridge that contains only the medication of a first user and at least one other cartridge that contains only the medication of a second user.

15. A method of dispensing a medication to a user, comprising the steps of:
inserting at least one cartridge into at least one of a plurality of cartridge slots within a housing of a medication dispensing device, the at least one cartridge including a stationary hub and a rotational wheel, the stationary hub having that is located along a central axis about which the rotational wheel can rotate that is received in a similarly shaped opening of the respective cartridge slot to orient a window of the stationary hub in a vertically downward direction and to hold the window in the vertically downward direction as the rotational wheel rotates about the central axis, the rotational wheel including a plurality of circumferentially spaced apart chambers containing medication doses, and the at least one cartridge including a chip that includes data that is encrypted such that only the medication dispensing device associated with the user can read the data;

decrypting and reading the data contained on the chip of the at least one cartridge and storing in a memory of the medication dispensing device information related to the medication doses;

receiving with a processor an instruction to dispense a medication dose from the at least one cartridge; and rotating the rotational wheel of one of the cartridges with a drive mechanism to vertically align one of the chambers with a medication drop door causing the medication dose in the chamber that is now aligned with the medication drop door to fall out of the cartridge.

16. The method as set forth in claim 15 further including the step of verifying an identity of a user after the step of receiving the instruction with the processor and wherein the step of rotating the rotational wheel is proceeded to only in response to a positive verification of the identity of the user.

17. The method as set forth in claim 16 wherein the step of inserting at least one cartridge into one of a plurality of cartridge slots is further defined as inserting at least two cartridges into at least two cartridge slots.

18. The method as set forth in claim 17 wherein at least one of the cartridges is associated with a first user and at least one of the cartridges is associated with a different second user and wherein the step of verifying the identity of the user includes verifying that the user is the user associated with the cartridge to be dispensed from.

19. The method as set forth in claim 16 wherein the step of verifying the identity of the user includes verifying the identity of the user using at least one fingerprint or facial identification sensor on the external device.

20. The method as set forth in claim 19 wherein the step of verifying the identity of the user includes verifying the identity of the user using at least one fingerprint or facial identification sensor on a smart phone.

21. The method as set forth in claim 15 wherein the instruction to dispense a medication dose from one of the cartridges is according to an automatic dispensing schedule that is recorded in a memory of the medication dispensing device.

22. The method as set forth in claim 21 wherein the automatic dispensing schedule is stored into the memory from the data on the at least one cartridge.

23. The method as set forth in claim 15 wherein the step of inserting at least one cartridge at least one of a plurality of cartridge slots includes inserting at least one cartridge that contains only the medication of a first user and inserting at least one other cartridge that contains only the medication of a second user.

* * * * *